United States Patent
Cesura et al.

(10) Patent No.: US 7,101,917 B2
(45) Date of Patent: Sep. 5, 2006

(54) MITOCHRONDRIAL PERMEABILITY TRANSITION PORE AFFINITY LABELS AND MODULATORS

(75) Inventors: Andrea Cesura, Crans-pres-Celigny (CH); Emmanuel Pinard, Linsdorf (FR)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 10/817,975

(22) Filed: Apr. 5, 2004

(65) Prior Publication Data

US 2004/0220257 A1 Nov. 4, 2004

(30) Foreign Application Priority Data

Apr. 14, 2003 (EP) .................... 03008040

(51) Int. Cl.
*A61K 31/12* (2006.01)
(52) U.S. Cl. .................... 514/680; 435/4; 568/326
(58) Field of Classification Search ............. 514/680; 568/326; 435/4
See application file for complete search history.

(56) References Cited

U.S. PATENT DOCUMENTS 4,241,069 A 12/1980 Buckler et al.

FOREIGN PATENT DOCUMENTS

| EP | 0 117 412 | 8/1984 |
| EP | 0 118 685 | 9/1984 |
| EP | 0 456 183 A2 | 11/1991 |

OTHER PUBLICATIONS

Cesura, AM et al., 'The Voltage-dependent Anion Channel Is the Target for a New Class of Inhiitirs of the Mitochondrial Permeability Transition Pore' J. Biol.Chem. 278(50) Dec. 12, 2003, pp. 49812-49818.*

Andres M. Cesura, et al., The Journal of Biological Chemistry, vol. 278, No. 50, pp. 49812-49818 (2003).
Frederick E. Ward, et al., Journal of Medicinal Chemistry, vol. 24, No. 9, pp. 1073-1077 (1981).
Brouillet , E. et al; Proc. Nat'l Acad. Sci., (1995), 92(15) pp. 7105-7109.
Cassarino, D. et al: Biochim. Biophys. Acta., (1999), 1453, pp. 49-62.
Kroemer, G. et al; Nature Medicine, (2000) 6(5) pp. 513-519.
Vander Heiden, M.G., et al; Nature Cell Biol. (1999) 1(8) pp. E209-16.
Marzo, T. et al; Science, (1998) 281(5385) pp. 2027-2031.
Nicholls, D.G, and Budd, S.L., Physiol. Rev., (2000) 80(1) pp. 315-360.
Bernardi, P., Physiol. Rev. (1999) 79(4), pp. 1127-1155.
Bernardi, P. et al, Eur. J. Biochem. (1999) 264(3), pp. 687-701.
Wallace, D., Science (1999) 283(5407) pp. 1482-1488.
Crompton, M. , Biochem. J., (1999) 341, pp. 233-249.
Ichas, F. et al; Cell, (1997) 89, pp. 1145-1153.
Shimizu, S., et al, Nature, (1999) 399, 483-487.
Bernardi, P. et al, Trends Biochem. Sci. (2001) 26(2) pp. 112-117.
Dhainaut, A. et al., J. Med. Chem. (1992), vol. 35, pp. 2481-2496.
Costantini, P. et al., (1995), Toxicology vol. 99, pp. 77-88.
Sims, N. R., (1990), J. Neurochem. vol. 55, pp. 698-707.
Chernyak, B. V. & Bernardi, P., (1996), Eur. J. Biochem. vol. 238, pp. 623-630.
Hoek, J. B. et al., (1980), J. Biol. Chem. vol. 255, pp. 1458-1464.

* cited by examiner

*Primary Examiner*—Amelia A. Owens
(74) *Attorney, Agent, or Firm*—George W. Johnston; Patricia S. Rocha-Tramaloni; Kimberly J. Prior

(57) ABSTRACT

Methods of utilizing compounds of general formulas I and II as modulators and affinity labels of the MPTP complex are elucidated. Furthermore, methods for modulating the activity of the MPTP complex, methods for determining the presence of a component of the MPTP complex, and methods for identifying an active agent that modulates the activity of the MPTP complex, specifically methods for identifying an active agent that modulates the activity of the MPTP complex by interacting with the VDAC1 component are identified. Moreover, novel compounds of general formulas I and II are disclosed.

14 Claims, 10 Drawing Sheets

A (a)

(b)

(c)

(d)

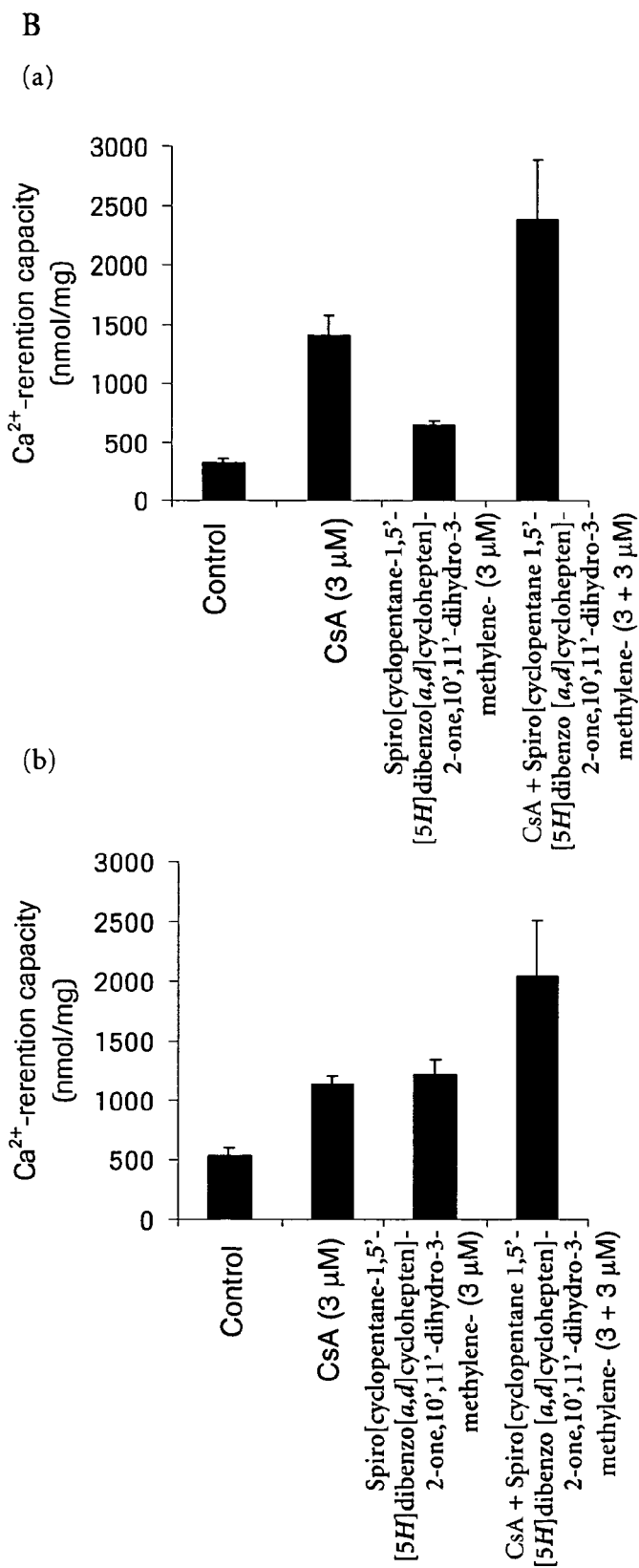

A

B

A

B

MITOCHRONDRIAL PERMEABILITY TRANSITION PORE AFFINITY LABELS AND MODULATORS

The present invention provides novel compounds useful as modulators and affinity labels of the mitochondrial permeability transition pore complex.

BACKGROUND OF THE INVENTION

Mitochondria play a pivotal role in cell survival and tissue development by virtue of their role in energy metabolism, regulation of cellular $Ca^{2+}$ homeostasis and apoptosis. Given this multifactorial role, regulation of cellular $Ca^{2+}$, metabolism, and bioenergetics function as an integrated system since energy conservation is used to drive each process. Mitochondrial energy conservation (ATP production) requires the respiration-driven formation of a proton electrochemical potential difference ($\Delta\mu H$) across the inner mitochondrial membrane (IMM), which is created by proton pumping by the respiratory complexes. Maintenance of the gradient demands a low permeability of the IMM to protons, charged species and solutes, whose fluxes are tightly controlled by specific carrier systems that are powered by the two components of the $\Delta\mu H$, i.e. the membrane potential difference ($\Delta\psi m$) and the $\Delta pH$. Yet, mitochondria in vitro can easily undergo an IMM permeability increase to solutes with molecular masses of about 1,500 Da or lower. This permeability change, called the permeability transition (PT), is regulated by the opening of a membrane pore, the mitochondrial permeability transition pore (MPTP). Long-lasting MPTP opening results in outer mitochondrial membrane (OMM) rupture and cytochrome c release, with ensuing dramatic consequences on mitochondrial function (e.g., collapse of $\Delta\mu H$, depletion of pyridine nucleotides) that lead to respiratory inhibition. This process has long been studied then, as a target for mitochondrial dysfunction in vivo, particularly in the context of specific human pathological events like ischemia-reperfusion injury and neurodegeneration. The MPTP has also drawn attention as a mediator of programmed cell death (apoptosis) and target of the action of BCL2 family members through the release of cytochrome c (Bernardi, P., Mitochondrial transport of cations: channels, exchangers, and permeability transition. Physiol Rev, 1999. 79(4): p. 1127–55; Nicholls, D. G. and S. L. Budd, Mitochondria and neuronal survival. Physiol Rev, 2000. 80(1): p. 315–60; Bernardi, P., et al., Mitochondria and cell death. Mechanistic aspects and methodological issues. Eur J Biochem, 1999. 264(3): p. 687–701; Bernardi, P., et al., A mitochondrial perspective on cell death. Trends Biochem Sci, 2001. 26(2): p. 112–7).

It is currently agreed that mitochondria play an important role in controlling life and death of cells (apoptosis; Kroemer G & Reed J C, Mitochondrial control of cell death. Nat Med. 2000, 6(5): 513–9). It appears both that an increasing number of molecules involved in the transduction of the signal and also many metabolites and certain viral effectors act on mitochondria and influence the permeabilisation of mitochondrial membranes. Cytoprotective molecules may be used, thanks to their ability to stabilize mitochondrial membranes, in the treatment of illnesses where there is excessive apoptosis (neurodegenerative diseases, ischemia, AIDS, fulminant hepatitis, etc.).

A change in mitochondrial membrane permeability is a key event of apoptotic cell death associated with the release of caspase activators and caspase-independent death effectors from the intermembrane space, dissipation of the inner transmembrane potential, as well as a perturbation of oxidative phosphorylation (Kroemer G & Reed J C, Mitochondrial control of cell death. Nat Med. 2000, 6(5):513–9; Vander Heiden M G & Thompson C B, Bcl-2 proteins: regulators of apoptosis or of mitochondrial homeostasis?, Nat Cell Biol. (1999) 1(8):E209–16; Wallace D C, Mitochondrial diseases in man and mouse. Science (1999); 283 (5407), 1482–8). Pro-and anti-apoptotic members of the Bcl-2 family regulate inner and outer mitochondrial membrane permeability through interactions with the adenine nucleotide translocase (ANT; in the inner membrane), the voltage-dependent anion channel (VDAC; in the outer membrane), and/or through autonomous channel-forming activities (Kroemer G & Reed J C, 2000; Marzo I, Brenner C, Zamzami N, Jurgensmeier J M, Susin S A, Vieira H L, Prevost M C, Xie Z, Matsuyama S, Reed J C, Kroemer G., Bax and adenine nucleotide translocator cooperate in the mitochondrial control of apoptosis. Science, (1998), 281 (5385): 2027–31; Shimizu S., Narita M., Tsujimoto Y., Nature (1999), 399, 483–487; Vander Heiden & Thompson, 1999). ANT and VDAC are believed to be major components of the mitochondrial permeability transition pore (MPTP) complex, a polyprotein structure organized at sites at which the two mitochondrial membranes are in close vicinity (Crompton M., Biochem J (1999), 341, 233–249).

The mitochondrial permeability transition pore is a polyprotein complex formed in the contact site between the inner and the outer mitochondrial membranes that participate in the regulation of mitochondrial membrane permeability. It is composed of a set of proteins including mitochondrion-associated hexokinase (HK), porin (voltage-dependent anion channel or VDAC), adenine nucleotide translocation (ANT), peripheral benzodiazepine receptor (PBR), creatine kinase (CK), and cyclophilin D, as well as Bcl-2 family members. In physiological conditions, MPTP controls the mitochondrial calcium homeostasis via the regulation of its conductance by the mitochondrial pH, the mitochondrial membrane potential $\Delta\Psi_m$, NAD/NAD(P)H redox equilibrium and matrix protein thiol oxidation (Shimizu S., Narita M., Tsujimoto Y., Nature (1999), 399, 483–487; Crompton M., Biochem J 341,233–249 (1999); Ichas F., Jouaille L., Mazat J., Cell (1997), 89, 1145–53). MPTP has been implicated in many examples of apoptosis due to its capacity to integrate multiple pro-apoptotic signal transduction pathways and due to its control by proteins from Bcl-2/Bax family. The Bcl-2 family comprises death inhibitory (Bcl-2-like) and death inducing (Bax-like) members which respectively prevent or facilitate MPTP opening. Bax and Bcl-2 reportedly interact with VDAC and ANT within MPTP.

Apoptosis and related forms of controlled cell death are involved in a great number of illnesses. Excess or insufficiency of cell death processes are involved in auto-immune and neurodegenerative diseases, cancers, ischemia, and pathological infections or diseases such as viral and bacterial infections. In the area of neurodegenerative diseases, a great many observations suggest close links with mitochondrial control of apoptosis (see Kroemer G & Reed J C, Mitochondrial control of cell death. Nat Med. (2000), 6(5): 513–9). The neurotoxin-methyl-4-phenylpyridinium induces mitochondrial permeability transition and the exit of cytochrome c (Cassarino D S, Parks J K, Parker W D Jr, Bennett J P Jr. The parkinsonian neurotoxin MPP+ opens the mitochondrial permeability transition pore and releases cytochrome c in isolated mitochondria via an oxidative mechanism. Biochim Biophys Acta 1999;1453, 49–62).

Poisoning by mitochondrial toxins such as nitro-propionic acid or rotenone provokes in primates and rodents a Huntington-disease type of illness (Brouillet E, Hantraye P, Ferrante R J, Dolan R, Leroy-Willig A, Kowall N W, Beal M F., Chronic mitochondrial energy impairment produces selective striatal degeneration and abnormal choreiform movements in primates. Proc Natl Acad Sci USA. 1995 Jul 18;92(15):7105–9; Betarbet R, Sherer T B, MacKenzie G, Garcia-Osuna M, Panov A V, Greenamyre J T. Chronic systemic pesticide exposure reproduces features of Parkinson's disease Nat Neurosci. 2000, 1301–6).

In physiological conditions, ANT is a specific antiporter for ADP and ATP. However, ANT can also form a lethal pore upon interaction with different pro-apoptotic agents, including $Ca^{2+}$, atractyloside, HIV-Vpr-derived peptides and pro-oxidants. Mitochondrial membrane permeabilization may also be regulated by the non-specific VDAC pore modulated by Bcl-2/Bax-like proteins in the outer membrane and/or by changes in the metabolic ATP/ADP gradient between the mitochondrial matrix and the cytoplasm.

Although the relevance of the MPTP has gained wide recognition for its role in necrotic and apoptotic cell death, much of the information on its molecular identity still relies on indirect evidence. Also, lack of specific high-affinity probes for its components has hindered progress in the field.

More particularly, there exists a need in the art for methods and reagents for investigating and modulating mitochondrial permeabilization and apoptosis.

SUMMARY OF THE INVENTION

The present invention therefore provides a new class of compounds for the labeling and modulation of MPTP in the sub μM range. Moreover, the present invention provides the identification of the isoform 1 of VDAC (VDAC1) as a MPTP component and as the molecular target of these compounds.

The present invention provides the use of compounds of general formula I and compounds of general formula II as modulators and affinity labels of the MPTP complex. Furthermore, the present invention provides methods for modulating the activity of the MPTP complex, methods for determining the presence of a component of the MPTP complex, and methods for identifying an active agent that modulates the activity of the MPTP complex, specifically methods for identifying an active agent that modulates the activity of the MPTP complex by interacting with the VDAC1 component. Moreover, novel compounds of general formula I and of general formula II are provided by the present invention.

[cyclopentane-1,5'-[5H]dibenzo[a,d]cyclohepten]-2-one, 10',11'-t$_2$-10',11'-dihydro-3-methylene- were injected into a hydrohyapatite FPLC column. Elution was performed at 0.5 ml/min with a linear gradient of sodium phosphate buffer, pH 6.8 (up to 250 mM in 25 min, and then up to 400 mM in 5 min), and 1 min fractions were automatically collected. The histogram shows the radioactivity elution profile after counting an aliquot (5 μl) of the fractions. The inset shows the silver staining of Triton X-100 solubilised mitochondria (starting material, lane a); and of column flow-through (fractions 7 to 9, lane b). The fluorogram of the corresponding purified material is shown in lane c.

Figure 5:
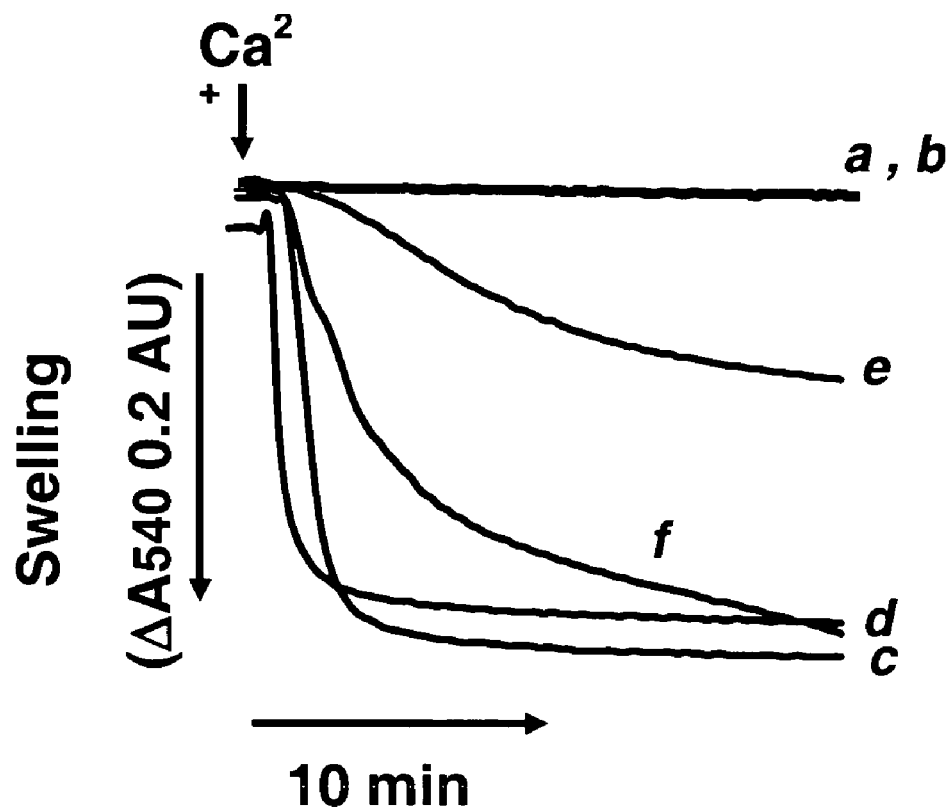
FIG. 5: Effect of $Ub_5$ on inhibition of MPTP by Spiro[cyclopentane-1,5'-[5H]dibenzo[a,d]cyclohepten]-2-one, 10',11'-dihydro-3-methylene-. (A) $Ca^{2+}$-induced swelling in rat liver mitochondria. Experimental conditions were as in FIG. 2, except that 60 μM $Ca^{2+}$ was added to induce the MPTP. In traces a and b no $Ca^{2+}$ was added with 50 μM $Ub_5$ present in b. For other traces, 60 μM $Ca^{2+}$ was added either alone, c, or in the presence of 50 μM $Ub_5$, d, 300 nM Spiro[cyclopentane-1,5'-[5H]dibenzo[a,d]cyclohepten]-2-one,10',11'-dihydro-3-methylene-,e, and 300 nM Spiro[cyclopentane-1,5'-[5H]dibenzo[a,d]cyclohepten]-2-one,10', 11'-dihydro-3-methylene-and 50 μM $Ub_5$, f. Compounds were added ~5 min before $Ca^{2+}$. (B) $Ca^{2+}$-induced depolarisation of rat brain mitochondria. The medium used was as in the legend to FIG. 4, except that 0.5 μM Rhodamine-123 was added instead of Calcium Green-5N, and MPTP was induced by addition of 20 μM $Ca^{2+}$. Trace a, control ($Ca^{2+}$ alone), b, 300 nM Spiro[cyclopentane-1,5'-[5H]dibenzo[a,d]cyclohepten]-2-one,10',11'-dihydro-3-methylene-, c, 300 nM Spiro[cyclopentane-1,5'-[5H]dibenzo[a,d]cyclohepten]-2-one,10',11'-dihydro-3-methylene- and 50 μM $Ub_5$.
Figure 5:
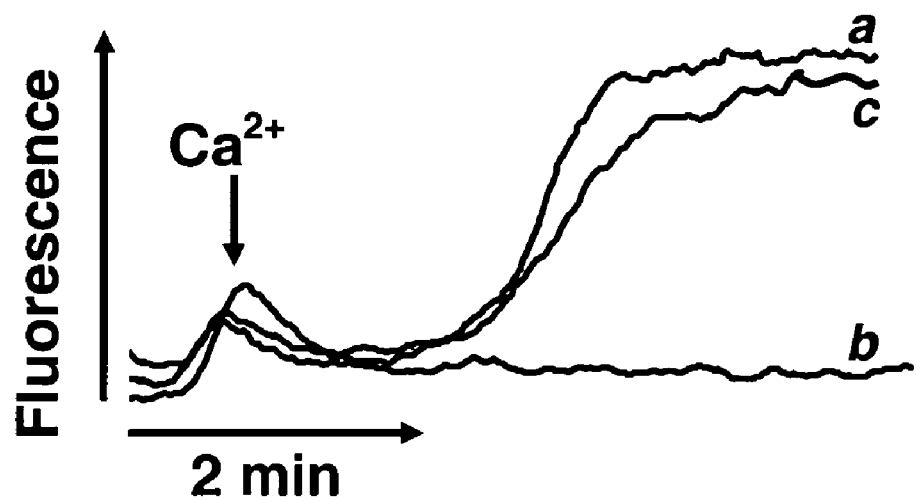
Figure 8:
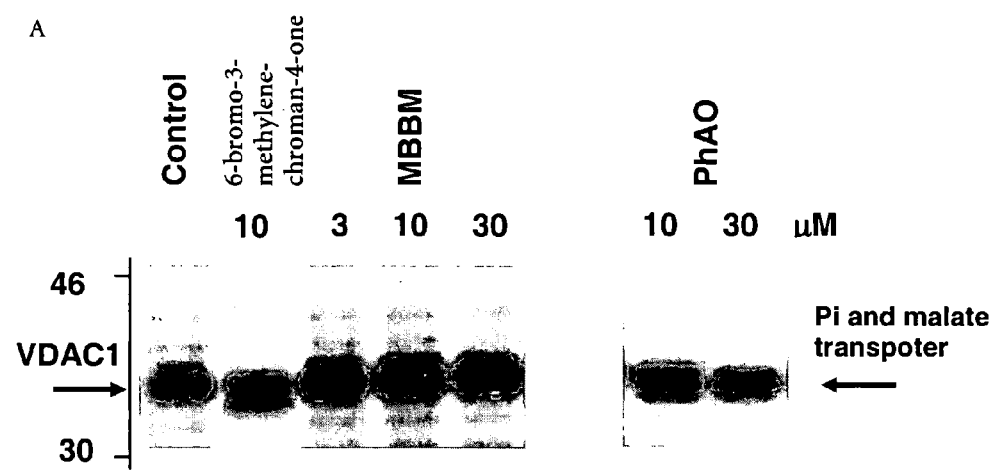
Figure 8:
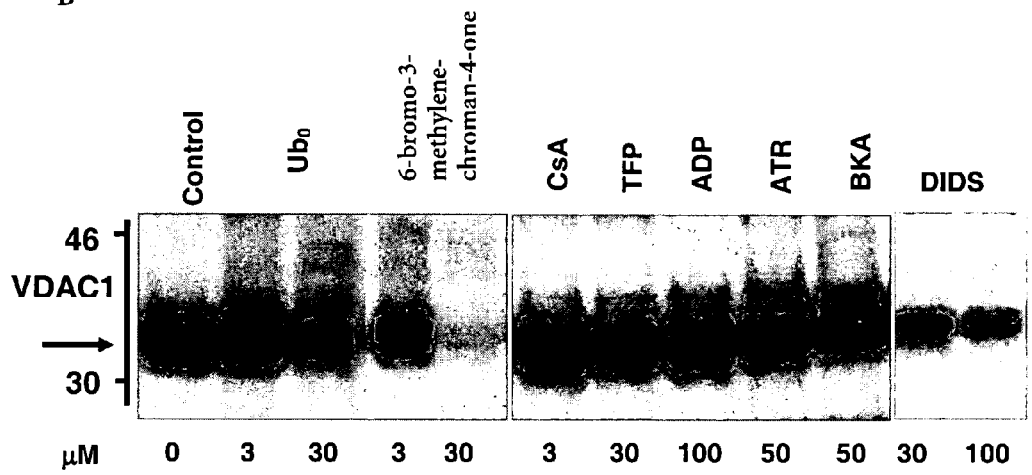

FIG. 8: (A) Effect of monobromobimano (MBBM) and phenylarsino oxide (PhAO) on VDAC1 labeling by Spiro [cyclopentane-1,5'-[5H]dibenzo[a,d]cyclohepten]-2-one, 10',11'-t$_2$-10',11'-dihydro-3-methylene- in rat brain mitochondria. Experimental conditions were as in the legend to FIG. 5. (B) Effect of various MPTP inhibitors, atractyloside (ATR) and DIDS on VDAC1 labeling by Spiro[cyclopentane-1,5'-[5H]dibenzo[a,d]cyclohepten]-2-one,10',11'-t$_2$-10',11'-dihydro-3-methylene- in rat brain mitochondria. Mitochondria were exposed to DIDS for 5 min before rinsing for removal of the free agent and labeling with Spiro[cyclopentane-1,5'-[5H]dibenzo[a,d]cyclohepten]-2-one,10',11'-t$_2$-10',11'-dihydro-3-methylene.

Figure 9:
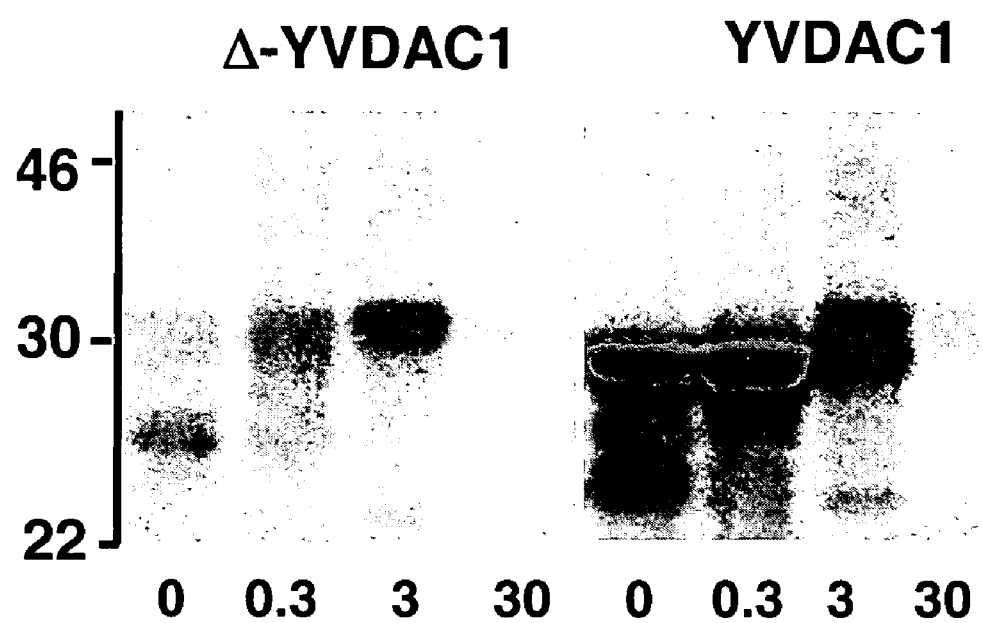

FIG. 9: Spiro[cyclopentane-1,5'-[5H]dibenzo[a,d]cyclohepten]-2-one,10',11'-t$_2$-10',11'-dihydro-3-methylene affinity labeling of yeast mitochondria lacking the por1 gene for YVDAC1 (Δpor1) and into Δpor1 yeast mitochondria transfected with YVDAC1 in presence or absence of different concentrations of Spiro[cyclopentane-1,5'-[5H]dibenzo[a,d] cyclohepten]-2-one,10',11'-dihydro-3-methylene (unlabeled). The fluorograms of gels after SDS-PAGE are shown. Mitochondria isolated from yeast strains were incubated in the presence of 10 nM Spiro[cyclopentane-1,5'-[5H]dibenzo [a,d]cyclohepten]-2-one,10',11'-t$_2$-10',11'-dihydro-3-methylene for 15 min at 25° C. Numbers indicate the concentrations (μM) of the various compounds added.

DETAILED DESCRIPTION OF THE INVENTION

The present invention provides a method of modulating the activity of the MPTP complex comprising exposing said complex to a compound comprising a) general formula I,

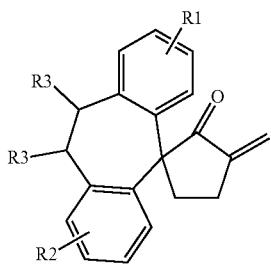

I wherein R1 and R2 are selected from the group consisting of H, halogen, alkyl, cycloalkyl, and alkoxy; and R3 is selected from the group consisting of H, D, and T or b) general formula II,

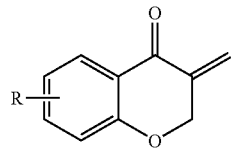

II wherein R is selected from the group consisting of H, halogen, alkyl, cycloalkyl, and alkoxy.

Preferred methods involve the use of the compounds of general formula I and especially more preferred is the use of the compounds of general formula I, wherein R1 and R2 are H, and R3 is H. Also preferred is the use of the compounds of general formula II, wherein R is H, Br, Cl or Cl$_2$ or wherein R is H or a cycloalkyl.

A modulator of the activity of the MPTP complex of the present invention is a compound that inhibits, diminishes, or enhances the activity of the MPTP. By activity of the MPTP it is understood a change in permeability of the inner mitochondrial membrane due to a transition of the pore-forming unit from a closed to an open state or vice versa.

Moreover, the present invention provides a method of using a compound as an affinity label for a compound of the MPTP complex comprising exposing said complex to a compound of a) general formula I, wherein R1 and R2 are selected from the group consisting of H, T, halogen, alkyl, cycloalkyl, and alkoxy; and R3 is selected from the group consisting of H, D, and T, and wherein at least one of the residues R1, R2 and R3 further comprises at least one radioisotope or a compound of b) general formula II, wherein R is selected from the group consisting of T, halogen, alkyl, cycloalkyl, alkoxy; wherein R further comprises at least one radioisotope.

Preferred methods involve the use of the compounds of general formula I and especially more preferred is the use of the compounds of general formula I, wherein R1 and R2 are H, and R3 is H. Also preferred is the use of the compounds of general formula II, wherein R is H, Br, Cl or Cl$_2$ or wherein R is H or a cycloalkyl.

Preferred methods involve the use of the above-described compounds as an affinity label for the VDAC1 component of the MPTP complex. Preferred methods involve the use of the compounds of general formula I and especially more preferred is the use of the compounds of general formula I, wherein R1 and R2 are H, and R3 is H. Also preferred is the use of the compounds of general formula II, wherein R is H or Br or wherein R is H or a cycloalkyl.

In a further embodiment, the present invention provides a method for modulating the activity of a MPTP complex comprising 1) exposing a cell or tissue in a biological sample to a compound comprising a) general formula I as described above, wherein R1 and R2 are selected from the group consisting of H, halogen, alkyl, cycloalkyl, and alkoxy, and R3 is selected from the group consisting of H, D, and T or b) general formula II as described above, wherein R is selected from the group consisting of H, halogen, alkyl, cycloalkyl and alkoxy, and 2) measuring the activity of the MPTP complex compared to its activity in the absence of the compound.

As used herein, "biological sample" comprises all samples of tissue, cells and body fluid taken from an animal or a human being, comprising mitochondria comprising the MPTP complex.

Methods for determining or measuring the activity of the MPTP complex are known in the art and comprise measuring swelling and shrinkage of mitochondria induced by $Ca^{2+}$ or other agents, measuring of radiolabeled sucrose uptake, measuring of $Ca^{2+}$-retention capacity of mitochondria, or measuring mitochondrial membrane potential using fluorescent probes or labelled or unlabeled lipophilic cations (Bernardi, P., et al., Mitochondria and cell death. Mechanistic aspects and methodological issues. Eur J Biochem, 1999. 264(3): p. 687–701).

In another embodiment, a method is provided for determining the presence of a component of a MPTP complex comprising:, contacting a biological sample of interest with a compound comprising a) general formula I, wherein R1 and R2 are selected from the group consisting of H, T, halogen, alkyl, cycloalkyl, and alkoxy; and R3 is selected from the group consisting of H, D, and T; and wherein at least one of the residues R1, R2 and R3 further comprises at least one radioisotope or b) general formula II, wherein R is selected from the group consisting of T, halogen, alkyl, cycloalkyl, and alkoxy; wherein R further comprises at least one radioisotope, under conditions to permit the binding of the compound to a component of the MPTP complex; and 2) detecting the binding of the compound; and 3) optionally quantifying the binding of the compound detected.

Binding of a compound to a component of the mitochondrial permeability transition pore complex may be determined under a variety of conditions comprising exposure of cultured cells or isolated mitochondria to labeled compound under physiological conditions and separation of unbound from bound compound by methods known in the art. Preferred are incubations of mitochondria isolated from tissues such as brain or liver with radiolabeled compound for a determined period of time. For the labeling reaction the mitochondria can be in a de-energized state, i.e. incubation in the absence of any respiratory substrates, or in an energized state when respiratory substrates such as succinate or glutamate/malate are present. The binding of a compound to a component of the MPTP complex may be quantified by measuring the radioactivity bound to the mitochondrial fraction. The quantification is facilitated by separating from free labeled affinity compound. The process of separating includes, but is not limited to washing, filtration and centrifugation. The process of separating is also intended to encompass homogenous techniques, for example scintillation proximity assay (SPA), where free labeled affinity compound in situ is not separated from bound labeled affinity compound. With the binding of the compound it is meant the total binding of the compound including specific and non-specific binding. Non-specific binding is assessed by competition with a saturating concentration of the same or another known compound. Specific binding of the affinity compound is then determined by subtracting the non-specific binding from the total binding of the affinity compound. If the radiolabeled compound forms a covalent bond with a component of the mitochondrial transition pore complex the mitochondrial protein can first be separated by sodium dodecyl sulfate gel electrophoresis and the radioactivity associated with protein bands determined by autoradiography.

A further embodiment provides a method for identifying an active agent that modulates the activity of a MPTP complex comprising:

contacting a biological sample of interest with a compound comprising a) general formula I, wherein R1 and R2 are selected from the group consisting of H, T, halogen, alkyl, cycloalkyl, and alkoxy; and R3 is selected from the group consisting of H, D, T, and wherein at least one of the residues R1, R2 and R3 further comprises at least one radioisotope or b) general formula II, wherein R is selected from the group consisting of T, halogen, alkyl, cycloalkyl, and alkoxy; wherein R further comprises at least one radioisotope, under conditions to permit the binding of the compound to a component of the MPTP complex; and 2) detecting the binding of the compound; and 3) optionally quantifying the binding of the compound detected.

The activity of a selected agent on the MPTP activity may be determined by comparing the activity of the MPTP measured in the presence and in the absence of said agent by methods as described above.

Furthermore, a method is provided for identifying an active agent that modulates the activity of a MPTP complex by interacting with VDAC1 comprising:

contacting a biological sample containing cells with VDAC1 of the MPTP with a compound comprising a) general formula I, wherein R1 and R2 are selected from the group consisting of H, T, halogen, alkyl, cycloalkyl, and alkoxy; and R3 is selected from the group consisting of H, D, and T; wherein at least one of the residues R1, R2 and R3 comprises at least one radioisotope or b) general formula II, wherein R is selected from the group comprising T, halogen, alkyl, cycloalkyl, and alkoxy; wherein R further comprises at least one radioisotope in the presence of a candidate agent; and 2) comparing the binding of the compound to VDAC1 of the MPTP in the presence of the candidate agent with the binding in the absence of said agent; and 3) optionally, testing the activity of said selected agent on the MPTP activity in a preparation of a cellular extract comprising subcellular elements with VDAC1 of the MPTP.

As used herein, "active agent" is intended to mean any compound that is being screened for modulating the activity of the MPTP complex. By modulating it is understood that the activity of the MPTP complex may be inhibited, may be diminished or may be enhanced. It is understood that an "active agent", which is active in the method of the invention for modulating the activity of the MPTP complex, can subsequently be used in pharmaceutical compositions for the treatment of a neurodegenerative disorder selected from the group consisting of Amyotrophic Lateral Sclerosis, Alzheimer's disease, Huntington's disease and Parkinson's disease or for the treatment of a neurological disorder selected from the group consisting of diabetic neuropathy, cerebral hypoxia, encephalitis and menengitis.

Calcium entry during an excitotoxic insult is an essential mediator of neuronal cell death. Mitochondrial dysfunction plays an important role in excitotoxic cell death. Inhibitors of MPTP have been reported to be neuroprotective: Cyclosporin A has been found to delay/reduce NMDA-induced mitochondrial membrane depolarization and cell death and to have neuroprotective effects in certain animal models (ischemia, hypoglycaemia, and brain trauma). N-Me-Val4-CsA, a CsA non-immunosuppressive analogue, has also been shown to have neuroprotective properties. Therefore, modulators, and especially inhibitors of MPTP may represent a novel neuroprotective therapeutic strategy (Murphy A N, Fiskum G, Beal M F., Mitochondria in neurodegeneration: bioenergetic function in cell life and death, J Cereb Blood Flow Metab. 1999 19,231–45; Tatton W G, Chalmers-Redman R M. Mitochondria in neurodegenerative apoptosis: an opportunity for therapy? Ann Neurol. 1998 44 (3 Suppl 1):S134–41).

The present invention also provides the active agents identified by the methods of the present invention as described above.

The compounds of general formula I, wherein R1 and R2 are selected from the group consisting of H, halogen, alkyl, cycloalkyl, and alkoxy; and R3 is selected from the group consisting of H, D, and T are novel.

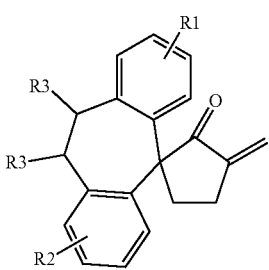

I

Preferred are compounds of general formula I, wherein R1 and R2 are H, and R3 is H. The described compounds may be used as modulators of the activity of the MPTP.

The compounds of formula II, specifically where R is H or a cycloalkyl are also novel.

The compounds of general formula I may be synthesized according to the depicted synthesis scheme:

Compounds of general formula I may be prepared in 3 steps from intermediate IV: hydrogenation, deuteration, or tritiation to provide saturated compound III followed by condensation with a secondary amine hydrochloride salt such as pyrrolidine hydrochloride salt to provide a Mannich adduct which is finally transformed to I under acidic condition by using for example silica gel as acid catalyst. Intermediate IV may be prepared using standard chemical transformations from compound VII as described in Denmark et al., Organic Synthesis, vol 74, 33: Treatment of VII with a base such as lithiumdiisopropylamine and 4-bromobutyronitrile provides VI which is then cyclised under basic condition to yield V. Acidic hydrolysis of V leads to intermediate IV. Starting material VII may be prepared following known procedures described by Regnier G. J., J. Med. Chem. 1992, 35, 2481–2496. Compounds of general formula I, wherein R1, R2 are radiolabels (D, T) may be prepared by deuteration or tritiation of compound III, wherein R1 and R2 being halogen to provide compound III, wherein R1 and R2 are D or T.

Some of the compounds of general formula II have been generally disclosed as plant growth inhibitors in EP118685 and EP117412 and can be synthesized as described therein. However, specific, preferred compounds of general formula II, wherein R is selected from the group consisting of H, T, D, halogen, alkyl, cycloalkyl, and alkoxy; can be used as modulators of the activity of the MPTP complex and are not disclosed. Preferred are the described compounds of formula II, wherein R is selected from the group consisting of H, Br, Cl and $Cl_2$.

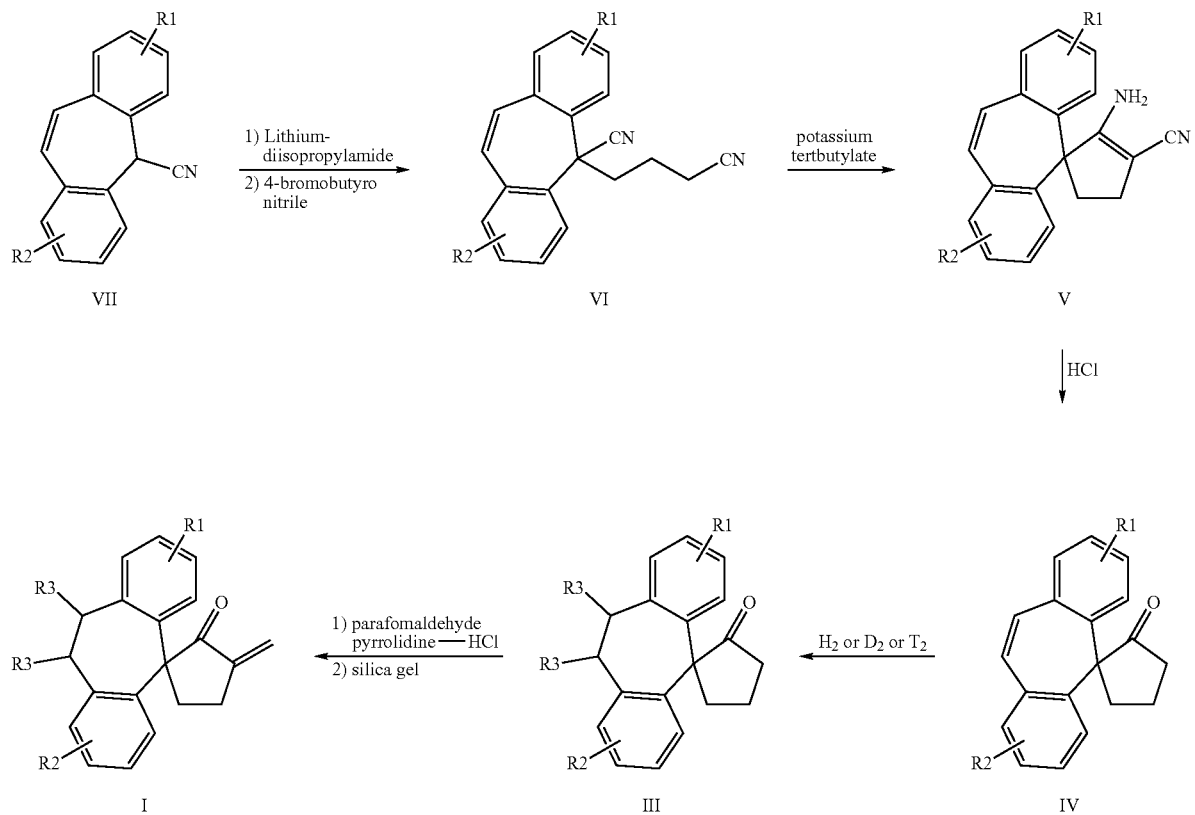

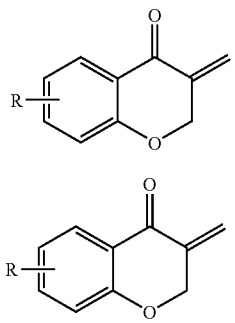

II

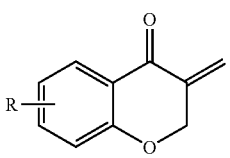

The compounds of general formula II, wherein R is selected from the group consisting of T, D, halogen, alkyl, cycloalkyl, and alkoxy, wherein R comprises at least one radioisotope, are specifically identified and claimed in the present invention. Preferred are the described compounds, wherein R comprises a T. Also preferred are the described compounds of formula II, wherein R is a radioisotope of Br, Cl or $Cl_2$. These compounds can be used as affinity label. Preferably, these compounds are used as an affinity label for a component of the MPTP complex.

As used herein, "affinity label" is intended to mean compounds with an affinity for a component of the MPTP in the range of micromolar concentrations or, preferably, lower, which are labeled with a radioisotope that is suitable for detection in an assay system or upon administration to a mammal. Suitable radioisotopes are known to those skilled in the art and include, for example, isotopes of halogens (such as chlorine, fluorine, bromine and iodine), and metals including technetium and indium. Preferred radioisotopes include $^3H$ and $^{14}C$. Most preferred is $^3H$. Radiolabeled compounds of the invention may be prepared using standard radiolabeling procedures well known to those skilled in the art. Suitable synthesis methodology has been described in detail.

Such radiolabeling should also be reasonably stable, both chemically and metabolically, applying recognized standards in the art. Also, although the compounds of the invention may be labeled in a variety of fashions with a variety of different radioisotopes, as those skilled in the art will recognize, such radiolabeling should be carried out in a manner such that the high binding affinity and specificity of the unlabeled affinity compound to a component of the MPTP is not significantly affected. By not significantly affected, it is meant that the binding affinity and specificity is not affected more than about 3 log units, preferably not more than about 2 log units, more preferably not more than about 1 log unit, even more preferably not more than about 500%, and still even more preferably not more than about 250%, and most preferably the binding affinity and specificity is not affected at all.

The radiolabeled affinity compound for a component of the MPTP may have a specific activity in the range of 500 mCi/mmole to 100 Ci/mmole. Preferably, it has a specific activity of 65 Ci/mmole. The bound radiolabeled affinity compound may be measured by addition of a scintillator.

Having now generally described this invention, the same will become better understood by reference to the specific examples, which are included herein for purpose of illustration only and are not intended to be limiting unless otherwise specified.

EXAMPLES

Commercially available reagents referred to in the examples were used according to manufacturer's instructions unless otherwise indicated. [$^3H$]-Tetraphenylphosphonium ([$^3H$]-TPP, 24–29 Ci/mmol) was purchased from Amersham Biosciences (Switzerland). CsA, TFP, ubiquinone$_0$ (Ub$_0$), ubiquinone$_5$ (Ub$_5$) were obtained from Sigma (Switzerland); atractyloside (ATR) and bongrekic acid (BKA) from BioMol (Anawa, Switzerland). Calcium-Green 5N (hexapotassium salt), Rhodamine-123 and 4,4'-diisothiocyanatostilbene-2,2'-disulfonic acid (DIDS, disodium salt) were from Molecular Probes (Juro, Switzerland).

Example 1

Screening Assay

In an attempt to identify new inhibitors of the MPTP, a compound library was screened using $Ca^{2+}$-induced swelling (in the presence Pi) of rat liver mitochondria energized with succinate (in the presence of 2 μM rotenone) as functional assay.

Liver and brain mitochondria were prepared from male Albino RoRo rats or MoRo mice (BRL, Fillinsdorf, Switzerland). For swelling experiments, liver mitochondria were isolated by differential centrifugation according to standard procedures (Costantini, P., Petronilli, V., Colonna, R. & Bernardi, P. (1995) Toxicology 99, 77–88). The mitochondrial pellet was resuspended in 250 mM sucrose buffered to pH 7.4 with 10 mM Tris HCl and kept in ice until use. Brain mitochondria from rat and mouse were obtained using a Percoll gradient according to the method described in (Sims, N. R. (1990) J. Neurochem. 55, 698–707). For affinity labeling experiments in liver mitochondria, organelles from this tissue were also isolated on a Percoll gradient. Protein content was determined using the Pierce bicichoninic acid protein assay kit.

$Ca^{2+}$-induced swelling (sucrose permeability) in energized mitochondria was assayed at 25° C. in 96 well-plates by measuring changes in absorbance at 540 nm by means of a SPECTRAMax 250 spectrophometer controlled by the SOFTmax PRO™ software (Molecular Devices, Switzerland). The incubation medium contained 0.2 M sucrose, 10 mM Tris-Mops, pH 7.4, 1 mM Pi-Tris, 5 μM EGTA. Succinate (5 mM, in the presence of 2 μM rotenone) or 5 mM glutamate/2.5 mM malate, buffered to pH 7.4 with Tris, were used as respiratory substrates. After a short (~5 min) preincubation in presence or absence of test compounds, mitochondrial swelling was induced by the addition of 20 μl $CaCl_2$ at final concentrations ranging from 40 to 80 μM, depending on respiratory substrates and $Ca^{2+}$ sensitivity of the mitochondrial preparation. The final incubation volume was 0.2 ml and the concentration of mitochondria was ~0.5 mg mitochondrial protein ml$^{-1}$. Swelling kinetics was followed for up to 30 min at 25° C. Absorbance readings were taken every 12 sec and the plate was shaken for 3 s between readings to ensure oxygen diffusion during the experiment and to avoid sedimentation of the mitochondria. Swelling experiments were also performed in fully deenergised liver mitochondria according to Chernyak, B. V. & Bernardi, P. (1996) Eur. J. Biochem. 238, 623–630.

Isolated liver mitochondria (~0.5 mg protein ml$^{-1}$) were incubated in a batch mode in the presence of 20 nM [$^3H$]TPP ([$^3H$]Tetraphenylphosphonium ([$^3H$]TPP, 24–29 Ci/mmol) from Amersham Biosciences, Switzerland) for 15 min at 25° C. Aliquots (100 μl) of the mixture were then distributed into 96-well plates containing 100 μl of the test compound and the incubation prolonged for 15 min at 25° C. Samples were then filtered through 0.3% (v/v) polyethyleneimmine-treated GF/B glass fiber filters using a 96-channel cell harvester and the filters washed twice with 1 ml of buffer. Fifty μl of MICROSCINT 40 (Packard) were then added to each well, before counting for radioactivity in a TopCount scintillation counter (Packard). Non-specific uptake was determined in the presence of 1 mM unlabeled TPP or 1 μM carbonyl-cianide-p-trifluoromethoxyphenyl hydrazone (FCCP). Mitochondrial oxygen consumption was measured polarographically at 25° C. using a Clark-type electrode.

Compounds found to inhibit MPTP where then counter-screened using uptake of the potentiometric probe [$^3$H]-TPP (Hoek, J. B., Nicholls, D. G. & Williamson, J. R. (1980) *J. Biol. Chem.* 255, 1458–1564) for determining in a semi-quantitative, but rapid way whether they interfered with mitochondrial respiration (e.g. protonophores). This allowed discarding of "false positives" which e.g. by lowering the mitochondrial membrane potential could lower $Ca^{2+}$-influx into mitochondria that is necessary for MPTP opening. Compounds that also did not interfere with mitochondrial respiration ($O_2$ consumption) at the concentrations inhibiting the MPTP were then selected for further characterization. Compounds with general formula I and compounds with general formula II have been identified in the screening. A number of compounds active with $EC_{50}$ in the sub μM range displayed common pharmacophoric elements such as enone as Michael acceptors.

Example 2

Spiro[cyclopentane-1,5'-[5H]dibenzo[a,d]cyclohepten]-2-one, 10',11'-dihydro-3-methylene

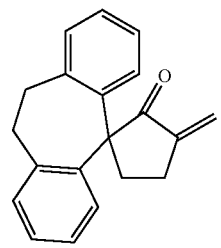

Spiro[cyclopentane-1,5'-[5H]dibenzo[a,d]cyclohepten]-2-one, 10',11'-dihydro-(0.3 g, 1.14 mmol), pyrrolidine hydrochloride (0.146 g, 1.37 mmol) and paraformaldehyde (0.1 g, 4.42 mmol) were dissolved in DMF (1 ml). The reaction mixture was immersed in a 80° C. oil bath, stirred for 2.5 hours under argon, and then the solvent was evaporated under high vacuum. The residue was taken in $MeCl_2$ and 1N NaOH was added. Aqueous phase was extracted with $MeCl_2$ and the combined organic phases were washed with water, dried with $Na_2SO_4$, concentrated in vacuo. The residue was dissolved in 4 ml $CH_2Cl_2$ and stirred at room temperature for 20 minutes in the presence of $SiO_2$ (1.3 g). After filtration, $SiO_2$ was washed with $CH_2Cl_2$. Filtrate was concentrated and the residue was chromatographed over silica gel (hexane-ethylacetate 48:02) to provide spiro[cyclopentane-1,5'-[5H]dibenzo[a,d]cyclohepten]-2-one, 10',11'-dihydro-3-methylene- (0.138 g, 44%) as a white solid, MS: m/e =274 (M$^+$).

Example 3

Spiro[cyclopentane-1,5'-[5H]dibenzo[a,d]cyclohepten]-2-one, 10',11'-$t_2$-10',11'-dihydro-3-methylene

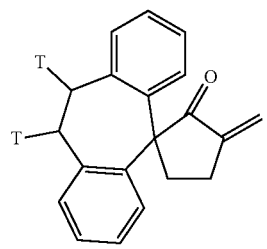

Spiro[cyclopentane-1,5'-[5H] dibenzo[a,d]cyclohepten]-2-one,10',11'-$t_2$-10',11'-dihydro- (2.2 Ci), pyrrolidine hydrochloride (3.5 mg, 0.033 mmol) and paraformaldehyde (3 mg, 0.1 mmol) were dissolved in DMF (0.1 ml). The reaction mixture was immersed in a 80° C. oil bath, stirred for 2.5 hours under argon, and then the solvent was evaporated under high vacuum. The residue was taken in $MeCl_2$ and 1N NaOH was added. Aqueous phase was extracted with $MeCl_2$ and the combined organic phases were washed with water, dried with $Na_2SO_4$, concentrated in vacuo. The residue was dissolved in 4 ml $CH_2Cl_2$ and stirred at room temperature for 2 hours in the presence of $SiO_2$ (200 mg). After filtration, filtrate was chromatographed on 1 g of Lichroprep Si60 25–40 μm (hexane-ethylacetate 48:02). The total activity of the purified product was 1.376 Ci and the specific activity as determined by mass spectrometry and the radiochemical purity were 65.1 Ci/mmole and 98.4%, respectively.

Example 4

Spiro[cyclopentane-1,5'-[5H]dibenzo[a,d]cyclohepten]-2-one,10',11'-dihydro

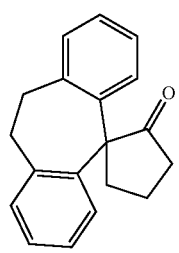

Spiro[cyclopentane-1,5'-[5H]dibenzo[a,d]cyclohepten]-2-one (0.02 g, 0.077 mmol) was dissolved in ethyl acetate (2 ml) and refluxed for 36 hours in the presence of Pd/C (0.01 g, 10% on carbon) under an atmospheric pressure of hydrogen. Catalyst was filtered and filtrate was evaporated. The residue was chromatographed over silica gel (hexane-ethylacetate 48:02) to provide spiro[cyclopentane-1,5'-[5H] dibenzo[a,d]cyclohepten]-2-one, 10',11'-dihydro- (0.017 g,z84%) as a colorless oil, MS: m/e=262 (M$^+$).

Example 5

Spiro[cyclopentane-1,5'-[5H]dibenzo[a,d]cyclohepten]-2-one,10',11'-t$_2$-10',11'-dihydro-Spiro[cyclopentane-1,5'-[5H]dibenzo[a,d]cyclohepten]-2-one (0.01 g, 0.034 mmol) was

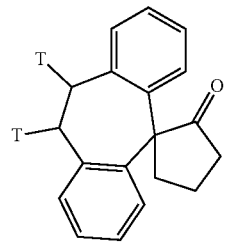

dissolved in DMF (0.8 ml) and heated at 80° C. for 3 hours in the presence of Pd/C (6 mg, 10% on carbon) under an atmospheric pressure of tritium. The crude product (2.5 Ci) was chromatographed onto a column of 1 g Lichroprep Si60, 25–40 μm (hexane-ethylacetate 48:02) to provide spiro[cyclopentane-1,5'-[5H]dibenzo[a,d]cyclohepten]-2-one, 10',11'-t$_2$-10',11'-dihydro- with a total activity of 2,2 Ci.

Example 6

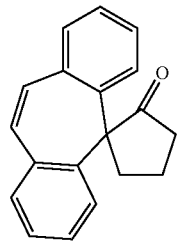

Spiro[cyclopentane-1,5'-[5H]dibenzo[a,d]cyclohepten]-2-one

2'-Aminospiro/5H-dibenzo<A,D>cycloheptene-5,1'-<2>-cyclopentene/-3'-carbonitrile (0.96 g, 3.38 mmol) was dissolved in dioxane (33 ml). Water (16 ml) and HCl (16 ml, 37%) were added. The reaction mixture was refluxed for 18 hours under argon, then cooled to room temperature and quenched with water and ethyl acetate. Aqueous phase was extracted with ethylacetate and the combined organic phases were washed with water, dried with Na$_2$SO$_4$ and concentrated in vacuo. The so obtained solid was stirred in hexane for 1 hour and filtered to provide spiro[cyclopentane-1,5'-[5H]dibenzo[a,d]cyclohepten]-2-one (0.324 g, 36%) as a white solid, MS: m/e=260 (M$^+$).

Example 7

2'-Aminospiro/5H-dibenzo<A,D>cycloheptene-5,1'-<2>-cyclopentene/-3'-carbonitrile

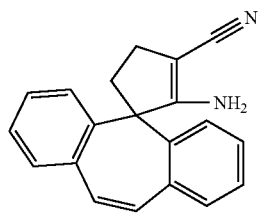

5-(3-Cyano-propyl)-5H-dibenzo[a,d]cycloheptene-5-carbonitrile (2 g, 7 mmol) was dissolved in THF (8 ml) and tBuOH (17 ml) and treated with tBuOK (0.78 g, 7 mmol). The reaction mixture was heated at 65° C. for 2 hours then cooled to room temperature and quenched with water and ether. Aqueous phase was extracted with ether and the combined organic phases were washed with water, dried with Na$_2$SO$_4$ and concentrated in vacuo. The residue was crystallized in CH$_2$Cl$_2$ at 0° C. to provide 2'-aminospiro/5H-dibenzo<A,D>cycloheptene-5,1'-<2>-cyclopentene/-3'-carbonitrile (0.47 g, 24%) as a white solid, MS: m/e=284 (M$^+$).

Example 8

5-(3-Cyano-propyl)-5H-dibenzo[a,d]cycloheptene-5-carbonitrile

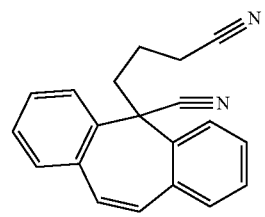

To a −5° C. solution of diisopropylamine (0.143 ml, 1 mmol) in THF (1 ml) was added dropwise nBuLi (0.67 ml, 1.06 mmol, 1.6 M in hexane). After 20 minutes stirring at −5° C., a solution of 5H-dibenzo[a,d]cycloheptene-5-carbonitrile (prepared according to: Regnier G. J. et al. J. Med. Chem. 1992, 35, 2481–2496) (0.2 g, 0.9 mmol) in THF (1 ml) was added dropwise. After 15 minutes at −5° C., a solution of 4-bromobutyronitrile (0.1 ml, 1 mmol) in THF (1 ml) was added slowly. The reaction mixture was allowed to warm up slowly to room temperature, stirred overnight and quenched with water and ether. Aqueous phase was extracted with ether and the combined organic phases were washed with water, dried with Na$_2$SO$_4$ and concentrated in vacuo. The residue was chromatographed over silica gel (hexane-ethylacetate 9:1) to provide 5-(3-cyano-propyl)-5H-dibenzo(a,d)cycloheptene-5-carbonitrile (0.2 g, 76%) as a colorless oil, MS: m/e=284 (M$^+$).

Example 9

Effect of Spiro[cyclopentane-1,5'-[5H]dibenzo[a,d]cyclohepten]-2-one,10',11'-dihydro-3-methylene- on Ca$^{2+}$-induced swelling in rat liver mitochondria. The incubation medium contained 0.2 M sucrose, 10 mM Tris-Mops, pH 7.4, 1 mM Pi-Tris, 5 μM EGTA and 5 mM glutamate/2.5 mM malate, buffered to pH 7.4 with Tris, as CPI respiratory substrates. After a short (~5 min) preincubation at 25° C. in presence of Spiro[cyclopentane-1,5'-[5H]dibenzo[a,d]cyclohepten]-2-one,10',11'-dihydro-3-methylene-, mitochondrial swelling was then induced by the addition of 40 μM CaCl$_2$ and MPTP opening monitored as the decrease in absorbance at 540 nm (FIG. 2).

Example 10

Figure 3:
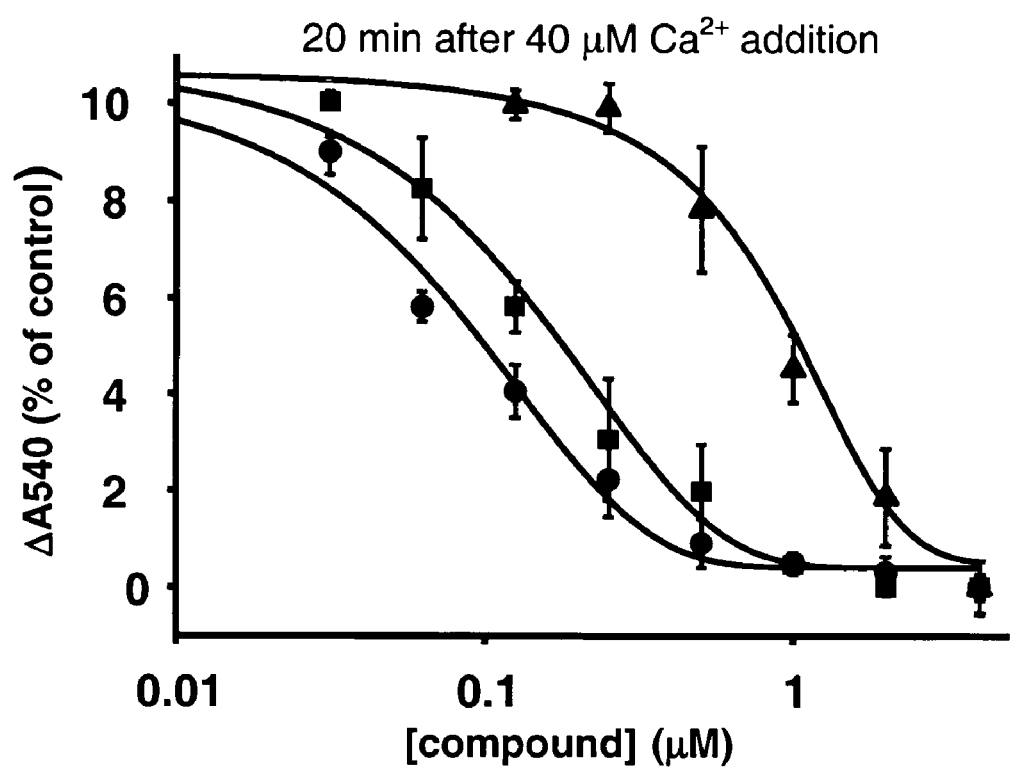
FIG. 3: Effect of Spiro[cyclopentane-1,5'-[5H]dibenzo[a,d]cyclohepten]-2-one,10',11'-dihydro-3-methylene-, its analogue 6-bromo-3-methylene-chroman-4-one and CsA on $Ca^{2+}$-induced swelling in rat liver mitochondria. Experimental conditions were as in FIG. 2. $EC_{50}$ values were determined as percentage changes in absorbance at 540 nm (ΔA540) versus baseline (no $CaCl_2$), 20 min after the addition of 40 μM $CaCl_2$ by fitting of the data to non-linear regression analysis using a four-parameters logistic equation using the SigmaPlot computer program. Values shown are means±SEM from 3 to 5 experiments in duplicate using different liver mitochondrial preparations.

Effect of Spiro[cyclopentane-1,5'-[5H]dibenzo[a,d]cyclohepten]-2-one,10',11'-dihydro-3-methylene-, 6-bromo-3-methylene-chroman-4-one and CsA on Ca$^{2+}$-induced swelling in rat liver mitochondria. Experimental conditions were as in Example 9. $EC_{50}$ values were determined as percentage changes in absorbance at 540 nm ($\Delta A540$) versus baseline (no $CaCl_2$), 20 min after the addition of 40 µM $CaCl_2$ by fitting of the data to non-linear regression analysis using a four-parameters logistic equation using the SigmaPlot computer program. Values shown are means±SEM from 3 to 5 experiments in duplicate using different liver mitochondrial preparations (FIG. 3, Table 1).

Figure 1:
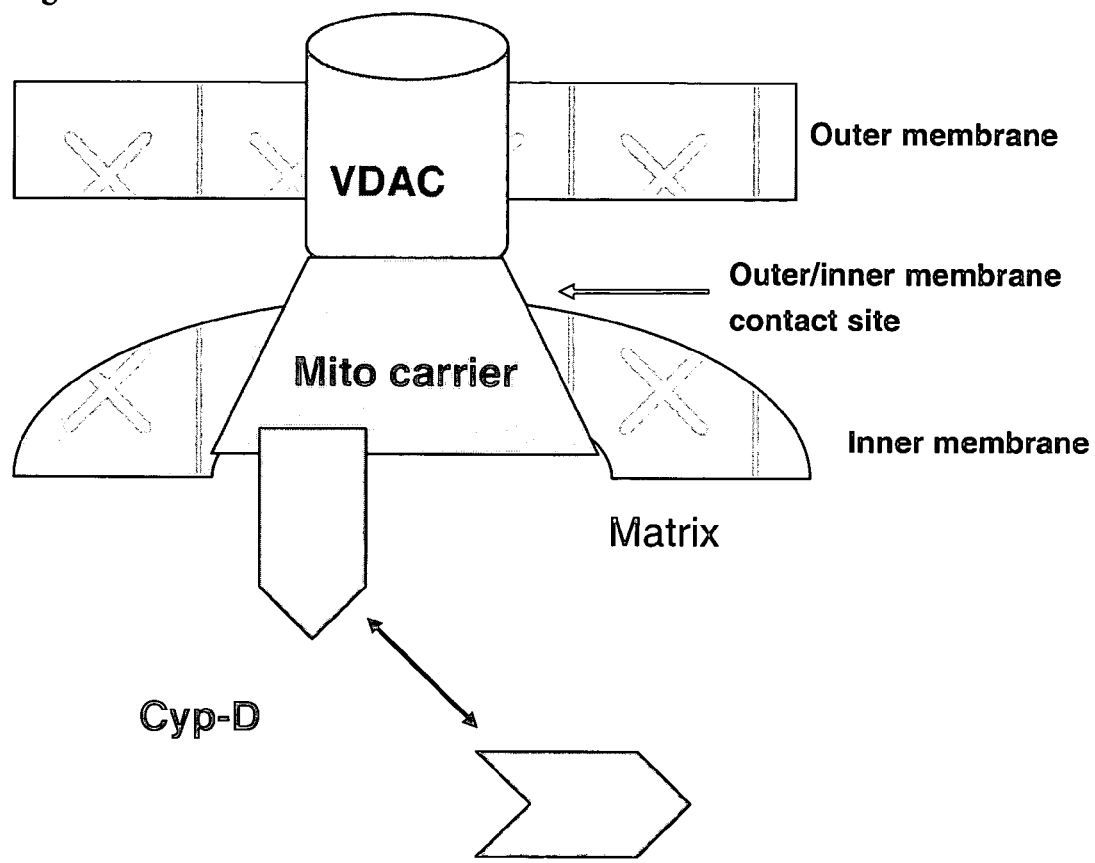
FIG. 1: Proposed schematic diagram for MPTP basic unit.
Figure 2:
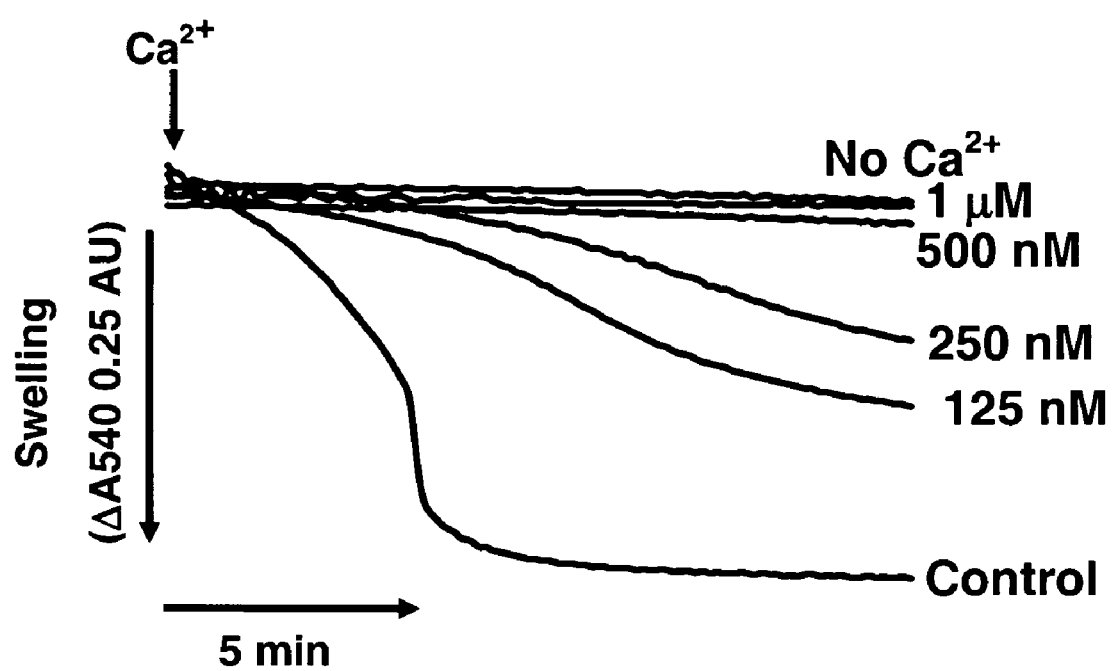
FIG. 2: Effect of Spiro[cyclopentane-1,5'-[5H]dibenzo[a,d]cyclohepten]-2-one,10',11'-dihydro-3-methylene- on $Ca^{2+}$-induced swelling in rat liver mitochondria. The incubation medium contained 0.2 M sucrose, 10 mM Tris-Mops, pH 7.4, 1 mM Pi-Tris, 5 μM EGTA and 5 mM glutamate/2.5 mM malate, buffered to pH 7.4 with Tris, as CPI respiratory substrates. After a short (~5 min) preincubation at 25° C. in presence of Spiro[cyclopentane-1,5'-[5H]dibenzo[a,d]cyclohepten]-2-one,10',11'-dihydro-3-methylene-, mitochondrial swelling was then induced by the addition of 40 μM $CaCl_2$ and MPTP opening monitored as the decrease in absorbance at 540 nm.

Spiro[cyclopentane-1,5'-[5H]dibenzo[a,d]cyclohepten]-2-one,10',11'-dihydro-3-methylene-potently inhibited $Ca^{2+}$-induced mitochondrial swelling (FIG. 2). Thus, Spiro[cyclopentane-1,5'-[5H]dibenzo[a,d]cyclohepten]-2-one,10', 11'-dihydro-3-methylene-inhibited MPTP opening in liver mitochondria energized with NADH-linked substrates (glutamate/malate) with an $EC_{50}$ of 98±10 (FIG. 3). Under similar conditions, CsA and the enone analogue 6-bromo-3-methylene-chroman-4-one displayed $EC_{50}$ of 160±9 and 930±30 nM, respectively. Table 1 shows the $EC_{50}$'s obtained in succinate-energized mitochondria for Spiro[cyclopentane-1,5'-[5H]dibenzo[a,d]cyclohepten]-2-one,10',11'-dihydro-3-methylene-, 6-bromo-3-methylene-chroman-4-one, 6-chloro-3-methylene-chroman-4-one, 6,8-dichloro-3-methylene-chroman-4-one in comparison to those of known MPTP inhibitors. Also under these experimental conditions Spiro[cyclopentane-1,5'-[5H]dibenzo[a,d]cyclohepten]-2-one,10',11'-dihydro-3-methylene-appeared to be at least as effective as CsA at inhibiting MPTP in liver mitochondria, and more potent than the other MPTP inhibitors tested. It is has to be reminded, however, that the $EC_{50}$'s reported are relative values and appear to be dependant on the amount of $Ca^{2+}$ added to induce swelling (as well as on respiratory substrates, see (Fontaine, E., Ichas, F., Bernardi, P. (1998) *J. Biol. Chem.* 273, 25734-25740). Still, the relative potencies of the various inhibitors were maintained varying the $Ca^{2+}$ load.

Spiro[cyclopentane-1,5'-[5H]dibenzo[a,d]cyclohepten]-2-one,10',11'-dihydro-3-methylene- and its analogue 6-bromo-3-methylene-chroman-4-one were also effective at inhibiting MPTP in deenergized mitochondria, a condition where interaction with sites indirectly modulating MPTP should be excluded (Linder, M. D., Morkunaite-Haimi, S., Kinnunen, P. K., Bernardi, P.& Eriksson, O. (2002) *J. Biol. Chem.* 277, 937–942) with $EC_{50}$ values of 0.37 and 2.8 µM, respectively (n=2, values determined 30 min after the addition of 200 µM $Ca^{2+}$). For comparison, the $EC_{50}$ of CsA and $Ub_0$ under this experimental condition, were found to be 0.22 and 4.9 µM. Spiro[cyclopentane-1,5'-[5H]dibenzo[a,d] cyclohepten]-2-one,10',11'-dihydro-3-methylene- also inhibited MPTP induced by phenylarsineoxide (25 µM) and by ATR (50 µM) therefore demonstrating that this compound is able to inhibit MPTP under a variety of induction conditions.

At concentrations completing blocking MPTP, Spiro[cyclopentane-1,5'-[5H]dibenzo[a,d]cyclohepten]-2-one,10', 11'-dihydro-3-methylene- and 6-bromo-3-methylene-chroman-4-one did not inhibit mitochondrial respiration (basal, ADP-induced and uncoupled), or Cyp-D peptidyl prolyl cis-trans isomerase enzymatic activity.

Example 11

Figure 4:
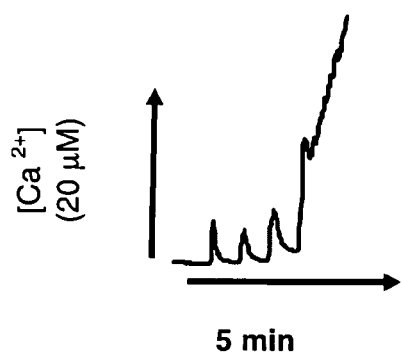
FIG. 4: (A) Effect of Spiro[cyclopentane-1,5'-[5H]dibenzo[a,d]cyclohepten]-2-one,10',11'-dihydro-3-methylene- and CsA on $Ca^{2+}$-retention capacity of rat brain mitochondria. The incubation medium contained 0.2 M sucrose, 10 mM Tris-Mops, pH 7.4, 1 mM Pi-Tris, 5 μM EGTA and 5 mM glutamate/2.5 mM malate, buffered to pH 7.4 with Tris, containing 0.01% (w/v) bovine serum albumin and 1 μM Calcium Green-5N. The final volume was 2.5 ml. Trace (a) control, (b) 1 μM CsA, (c) 1 μM Spiro[cyclopentane-1,5'-[5H]dibenzo[a,d]cyclohepten]-2-one,10',11'-dihydro-3-methylene- and (d) 1 μM CsA plus 1 μM Spiro[cyclopentane-1,5'-[5H]dibenzo[a,d]cyclohepten]-2-one,10',11'-dihydro-3-methylene-. Each fluorescence spike corresponds to addition of 5 μM $Ca^{2+}$. (B) Comparison of $Ca^{2+}$-retention capacity in liver (a) and brain mitochondria (b).
Figure 4:
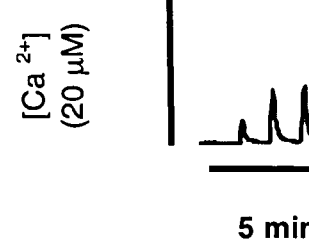
Figure 4:
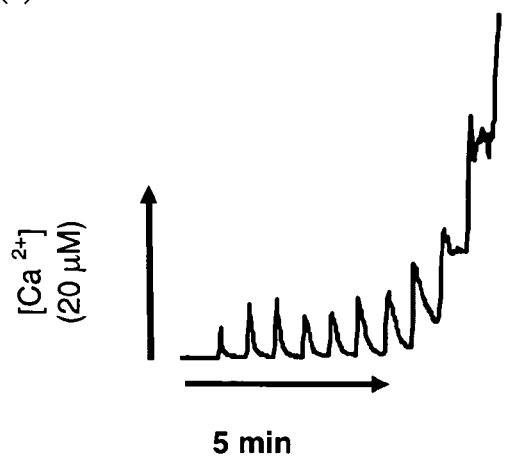
Figure 4:
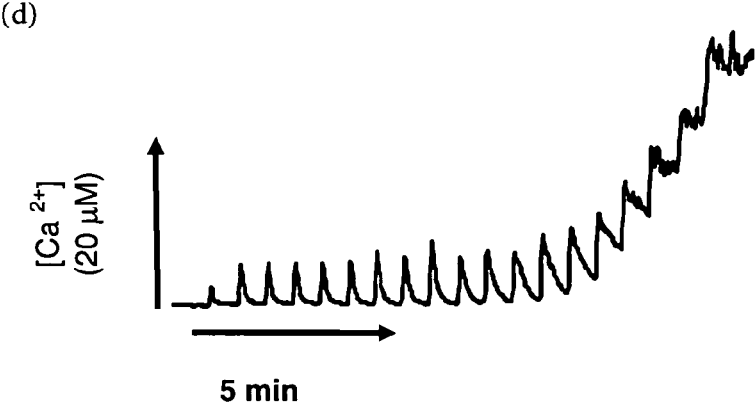

Effect of Spiro[cyclopentane-1,5'-[5H]dibenzo[a,d]cyclohepten]-2-one,10',11'-dihydro3-methylene- and CsA on $Ca^{2+}$-retention capacity of rat brain mitochondria (FIG. 4). Measurement of extramitochondrial $Ca^{2+}$ was determined using a Perkin-Elmer LS-50B fluorimeter controlled by the FL WinLab computer program. The incubation medium contained 0.2 M sucrose, 1 mM Pi -Tris, 10 mM Tris-MOPS, 5 mM glutamate-Tris, 2.5 mM malate-Tris, pH 7.4, containing 0.01% (w/v) BSA and 1 µM of the low affinity $Ca^{2+}$ indicator Calcium Green-5N (Fontaine, E., Eriksson, O., Ichas, F. & Bernardi, P. (1998) *J. Biol. Chem.* 273, 12662–12668). The final volume was 2.5 ml and the cuvette was thermostated at 25° C. Brain mitochondria were then subjected to a train of 5 µM $Ca^{2+}$ additions (~150 nmol mg proteins$^{-1}$). Extramitochondrial $Ca^{2+}$ was monitored at excitation/emission wavelengths of 505–535. Calibration of $Ca^{2+}$ signals was performed according to the manufacturer's instruction assuming a $Ca^{2+}$ $K_D$ for the dye of 14 µM. The $Ca^{2+}$-retention capacity in liver (a) and brain mitochondria (b) were also compared (FIG. 4B).

The effect of Spiro[cyclopentane-1,5'-[5H]dibenzo[a,d] cyclohepten]-2-one,10',11'-dihydro-3-methylene- at inhibiting MPTP was also investigated in mitochondria isolated from rat forebrain. Although the low yield of mitochondria from this tissue renders swelling experiments difficult to perform, Spiro[cyclopentane-1,5'-[5H]dibenzo[a,d]cyclohepten]-2-one,10',11'-dihydro-3-methylene- also inhibited swelling in brain mitochondria induced by addition of 80 µM $CaCl_2$ with potency in the range of that observed for liver mitochondria. Due to the difficulties mentioned above, the effect of Spiro[cyclopentane-1,5'-[5H]dibenzo[a,d]cyclohepten]-2-one,10',11'-dihydro-3-methylene- on MPTP in brain mitochondria was more accurately investigated by subjecting mitochondria isolated from rat forebrain to a series of $Ca^{2+}$ pulses (5 µM, ~150 nmol mg protein$^{-1}$) and by monitoring extramitochondrial $Ca^{2+}$ or using fluororescent probes. Under these conditions, mitochondria take up and retain $Ca^{2+}$ until the load reaches a threshold at which mitochondria undergo a process of fast $Ca^{2+}$ release, accompanied by depolarisation, effects which has been shown to be due to the opening of the MPTP. FIG. 4 shows the effect of CsA and Spiro[cyclopentane-1,5'-[5H]dibenzo[a,d]cyclohepten]-2-one,10',11'-dihydro-3-methylene- in these experiments. At 1 µM, (i.e. the maximal effective concentration observed for the compounds), both Spiro[cyclopentane-1, 5'-[5H]dibenzo[a,d]cyclohepten]-2-one,10',11'-dihydro-3-methylene- and CsA increased the ability of mitochondria to buffer $Ca^{2+}$, until a threshold was reached at which no $Ca^{2+}$ could be taken up. Both compounds approximately doubled the amount of $Ca^{2+}$ taken up by brain mitochondria. Thus, control mitochondria were able to accumulate 530±70 nmol Ca $^{2+}$/mg protein, whereas, in the presence of 1 µM CsA and Spiro[cyclopentane-1,5'-[5H]dibenzo[a,d]cyclohepten]-2-one,10',11'-dihydro-3-methylene-, the $Ca^{2+}$-bufering capacity increased up to 1130±80 and 1200±120 nmol $Ca^{2+}$mg protein$^{-1}$ respectively (Mean±SEM of 3 independent experiments). The combination of Spiro[cyclopentane-1,5'-[5H] dibenzo[a,d]cyclohepten]-2-one,10',11'-dihydro-3-methylene- and CsA (1 µM each) had an additive effect and mitochondria were able to accumulate up to 2050±450 nmol $Ca^{2+}$mg protein$^{-1}$. In agreement to the fact that Spiro [cyclopentane-1,5'-[5H]dibenzo[a,d]cyclohepten]-2-one, 10',11'-dihydro-3-methylene- does not inhibit Cyp-D activity, this indicates that Spiro[cyclopentane-1,5'-[5H]dibenzo [a,d]cyclohepten]-2-one,10',11'-dihydro-3-methylene- act at a site other than Cyp-D. As expected, no additive effect was observed in the presence of Spiro[cyclopentane-1,5'-[5H] dibenzo[a,d]cyclohepten]-2-one,10',11'-dihydro-3-methylene- and its analogue 6-bromo-3-methylene-chroman-4-one. Virtually identical results were obtained from experiments where $\Delta\psi_m$ was monitored after a series of $Ca^{2+}$ additions (5 µM each). Each $Ca^{2+}$ additions caused a reversible decreases in Δψ$_m$, until MPTP opening completely collapsed Δψ$_m$ and no further fluorescence increase could observed after addition of the protonophore FCCP. Also under these conditions, both Spiro[cyclopentane-1,5'-[5H]dibenzo[a,d]cyclohepten]-2-one,10',11'-dihydro-3-methylene- and CsA increased the number of Ca$^{2+}$ additions necessary to induce complete depolarization and an additive effect was observed after combining the two compounds. On the other hand, using the same procedures, testing of Spiro[cyclopentane-1,5'-[5H]dibenzo[a,d]cyclohepten]-2-one,10',11'-dihydro-3-methylene- in combination with other MPTP inhibitors, showed that the effect of Spiro[cyclopentane-1,5'-[5H]dibenzo[a,d]cyclohepten]-2-one,10',11'-dihydro-3-methylene- was additive with BKA, ADP, TFP and tamoxifen, thereby indicating a different site of action for Spiro[cyclopentane-1,5'-[5H]dibenzo[a,d]cyclohepten]-2-one, 10',11'-dihydro-3-methylene-. The only exception was Ub$_0$, a previously characterized MPTP blocker for which no such addit effect was seen.

The lack of additive effect with Ub$_0$, suggested that the binding site of Spiro[cyclopentane-1,5'-[5H]dibenzo[a,d]cyclohepten]-2-one,10',11'-dihydro-3-methylene-might correspond to the ubiquinone site reported to modulate MPTP opening by Fontaine & co-workers (Walter, L., Nogueira, V., Leverve, X., Heitz, M. P., Bernardi, P. & Fontaine, E. (2000) *J. Biol. Chem.* 275, 29521–29527). To further address this, it was investigated whether Ub$_5$, an ubiquinone derivative which has been shown to relieve the inhibitory effect of Ub$_0$, was also able to antagonize MPTP inhibition by Spiro[cyclopentane-1,5'-[5H]dibenzo[a,d]cyclohepten]-2-one, 10',11'-dihydro-3-methylene-. As shown in FIG. 5A for rat liver mitochondria, Ub$_5$ (50 μM) was able antagonize the inhibition by Spiro[cyclopentane-1,5'-[5H]dibenzo[a,d]cyclohepten]-2-one,10',11'-dihydro-3-methylene-, shifting Spiro[cyclopentane-1,5'-[5H]dibenzo[a,d]cyclohepten]-2-one,10',11'-dihydro-3-methylene- EC$_{50}$ from 290 nM to 2.4 μM (n=2, 60 μM Ca$^{2+}$, glutamate/malate as respiratory substrate). Also, in rat brain mitochondria (FIG. 5B), whereas 300 nM Spiro[cyclopentane-1,5'-[5H]dibenzo[a,d]cyclohepten]-2-one,10',11'-dihydro-3-methylene-inhibited Ca$^{2+}$-induced depolarisation, the inhibition was relieved by the presence of 50 μM Ub$_5$. Ub$_5$ alone had no effect. These results support the notion that Spiro[cyclopentane-1,5'-[5H]dibenzo[a,d]cyclohepten]-2-one,10',11'-dihydro-3-methylene- and ubiquinone derivatives may act at the same or functionally related sites on the MPTP.

Example 12

Affinity-labeling of mitochondria using Spiro[cyclopentane-1,5'-[5H]dibenzo[a,d]cyclohepten]-2-one, 10',11'-t$_2$-10',11'-dihydro-3-methylene Percoll purified mitochondria (~30 μg protein per sample) were incubated in the presence of 10 nM Spiro[cyclopentane-1,5'-[5H]dibenzo[a,d]cyclohepten]-2-one,10',11'-t$_2$-10',11'-dihydro-3-methylene- in a final volume of 200 μl. After incubation for 15 min at 25° C., samples were centrifuged at 25000×g and the mitochondrial pellet rinsed twice with buffer. Samples were then solubilized in sample buffer containing β-mercaptoethanol (1 h at 37° C.) and subjected to SDS-polyacrylamide gel-electrophoresis (SDS-PAGE) on Tris-glycine Novex pre-cast mini-gels (12% monomer concentration, Invitrogen BV, The Netherlands). After Coomassie Blue staining, gels were processed for fluorography by soaking in Amplify™ (Amersham Biosciences), drying and exposing to X-ray BioMax MS film with BioMax MS intensifying screen (Kodak) at −80° C. for the appropriate time.

Isolated mitochondria (Percoll gradient, ~5 mg proteins) were labeled in the presence of 20 nM Spiro[cyclopentane-1,5'-[5H]dibenzo[a,d]cyclohepten]-2-one,10',11'-t$_2$-10',11'-dihydro-3-methylene- for 15 min at 25° C. The mitochondrial pellet was then solubilized with 3 ml 3% Triton X-100 (Surfact-Amps X-100, Pierce) in 10 mM NaPO$_4$, pH 6.8, containing 0.5 mM phenylmethyl sulfonylfluoride (PMSF), 1 μg/ml leupeptin, 1.8/ml μg aprotinin and 1 μg/ml pepstatin A. Solubilized membrane were then injected into a ceramic hydroxyhapatite CHT-II 1×5 cm column (Bio-Rad, Switzerland) equilibrated in 10 mM NaPO$_4$, pH 6.8, containing 0.3% Triton X-100. The column was then eluted with a gradient of up to 400 mM NaPO$_4$, pH 6.8, containing 0.3% Triton X-100, at a flow rate of 0.5 ml min$^{-1}$. Fractions (1 min) were collected and an aliquot (5 μl) counted for radioactivity. Radioactive fractions were then subjected to SDS-PAGE, followed by staining and/or fluorography.

For the identification of the Spiro[cyclopentane-1,5'-[5H]dibenzo[a,d]cyclohepten]-2-one,10',11'-t$_2$-10',11'-dihydro-3-methylene-labeled protein(s), proteins in the radioactive chromatographic fractions were precipitated with trichloroacetic acid (20% final concentration). After reconstitution in SDS-PAGE sample buffer and carboxamidomethylation using iodoacetamide, proteins were submitted to SDS-PAGE. After staining with colloidal Coomassie Blue (Novex) and destaining, gel spots were excised and protein analyzed after in-gel digestion using modified trypsin (Promega), by matrix-assisted laser desorption ionisation-mass spectrometry (MALDI-MS) as previously described (Fountoulakis, M. & Langen, H. (1997) *Anal. Biochem.* 250, 153–156; Yoo, B. C., Fountoulakis, M., Cairns, N. & Lubec, G. (2001) *Electrophoresis* 22, 172–179). Samples were analyzed in a time-of-flight PerSeptive Biosystems mass spectrometer equipped with a reflector. The peptide masses obtained were matched with the theoretical peptide masses of all proteins from all species in the SWISS-PROT and TrEMBL database (http://us.expasy.org/sprot/). For protein search, monoisotopic masses were used and a mass tolerance of 0.0075% was allowed. Unmatched peptides or miscleaveage sites were not considered. The identity of some of the tryptic fragments was also confirmed by nano-electrospray tandem MS (Wilm, M. & Mann, M. (1996) *Anal. Chem.* 68, 1–8) by means of an API 365 triple quadruple mass spectrometer (Sciex, Toronto, Canada) as previously described (Krapfenbauer, K., Berger, M., Friedlein, A., Lubec, G. & Fountoulakis, M. (2001) *Eur J Biochem.* 268, 3532–3537).

Figure 6:
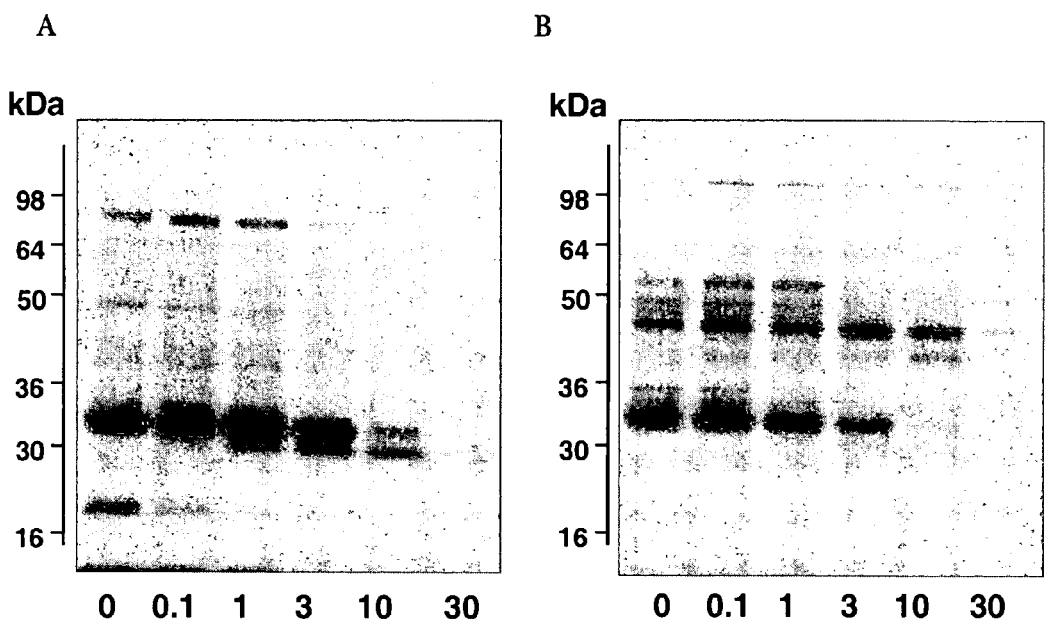
FIG. 6: Affinity-labeling of isolated rat brain (A) and liver (B) mitochondria. Mitochondrial preparations were incubated in the presence of 10 nM Spiro[cyclopentane-1,5'-[5H]dibenzo[a,d]cyclohepten]-2-one,10',11'-$t_2$-10',11'-dihydro-3-methylene- for 15 min at 25° C. in presence or absence of various concentrations of Spiro[cyclopentane-1,5'-[5H]dibenzo[a,d]cyclohepten]-2-one,10',11'-dihydro-3-methylene- (unlabeled). Samples were submitted to SDS-PAGE (see Experimental Procedures section for details) and fluorography. The fluorograms of the gels are shown. The molecular mass scale (kDa) is shown in the ordinate.

FIG. 6 shows the results obtained after labeling with 10 nM Spiro[cyclopentane-1,5'-[5H]dibenzo[a,d]cyclohepten]-2-one,10',11'-t$_2$-10',11'-dihydro-3-methylene- of intact mitochondria isolated from rat brain (panel A) and liver (panel B). A restricted number of proteins appeared to be labeled and, in both preparations, a protein of ~32 kDa appeared to be predominantly labeled. Increasing concentration of unlabeled Spiro[cyclopentane-1,5'-[5H]dibenzo[a,d]cyclohepten]-2-one,10',11'-dihydro-3-methylene-inhibited labeling of this band. This 32 kDa protein was a membrane protein, since no protein labeling was observed in mitochondria soluble fraction. A ~32 kDa band appeared to be predominantly labeled also using mitochondria isolated from mouse brain and liver from and SHSY-5Y human neuroblastoma cells. The presence of respiratory substrates (glutamata/malate or succinate/rotenone) did not alter the labeling pattern.

Figure 7:
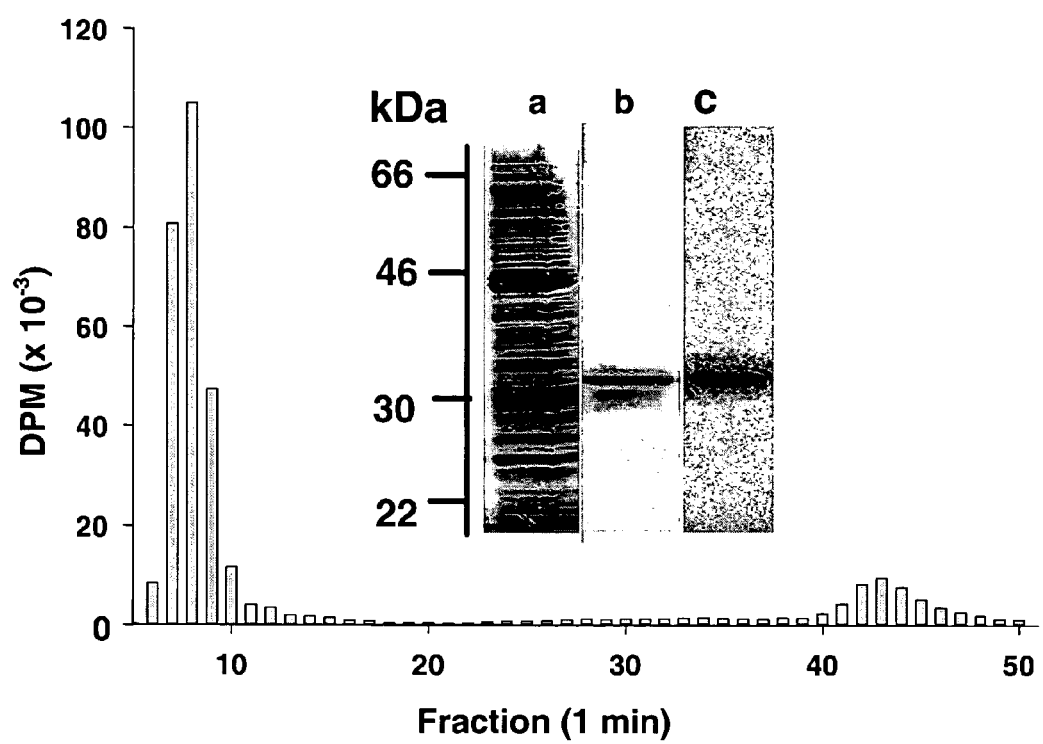
FIG. 7: Purification of the Spiro[cyclopentane-1,5'-[5H]dibenzo[a,d]cyclohepten]-2-one,10',11'-$t_2$-10',11'-dihydro-3-methylene- labeled 32 kDa protein. Triton X-100 solubilised mitochondria previously labeled with 20 nM Spiro

This protein from mitochondria prepared from the tissues mentioned above could be purified by a single FPLC chromatographic step using a hydroxyhapatite column. As shown in FIG. 7, the large majority of the radioactivity was not retained by the column, eluting in the column front. SDS-PAGE analysis of these fractions, followed by silver staining and fluorography, showed the presence of a major single protein (FIG. 7, insert). MALDI-MS analysis and nanoelectrospray tandem MS of tryptic fragments after in-gel digestion, indicated that the protein corresponded to the isoform 1 of VDAC (voltage-dependent anion-selective channel protein 1 or outer mitochondrial membrane protein porin 1, POR1_RAT, Q9Z2L0).

Example 13: Effect of monobromobimano and phenylarsino oxide on VDAC1 labeling by Spiro[cyclopentane-1,5'-[5H]dibenzo[a,d]cyclohepten]-2-one, 10',11'-t$_2$-10',11'-dihydro-3-methylene- in rat brain mitochondria. Experimental conditions were as in Example 12 (FIG. 8A). Effect of various MPTP inhibitors, atractyloside (ATR) and DIDS on VDAC1 labeling by Spiro[cyclopentane-1,5'-[5H]dibenzo[a,d]cyclohepten]-2-one, 10',11'-t$_2$-10',11'-dihydro-3-methylene- in rat brain mitochondria. Mitochondria were exposed to DIDS for 5 min before rinsing for removal of the free agent and labeling with Spiro[cyclopentane-1,5'-[5H]dibenzo[a,d]cyclohepten]-2-one,10',11'-t$_2$-10',11'-dihydro-3-methylene (FIG. 8B).

In order to correlate the labeling of VDAC1 with Spiro[cyclopentane-1,5'-[5H]dibenzo[a,d]cyclohepten]-2-one, 10',11'-t$_2$-10',11'-dihydro-3-methylene with the functional effects of this compound as a blocker of the MPTP, the effect of a number of MPTP inhibitors and the MPTP inducer ATR, on the labeling of VDAC1 by Spiro[cyclopentane-1,5'-[5H]dibenzo[a,d]cyclohepten]-2-one,10',11'-t$_2$-10',11'-dihydro-3-methylene in rat brain mitochondria was investigated. As shown in FIG. 8B, the incorporation of radioactivity was inhibited by the Spiro[cyclopentane-1,5'-[5H]dibenzo[a,d]cyclohepten]-2-one, 10',11'-dihydro-3-methylene-analogue 6-bromo-3-methylene-chroman-4-one (as well as by the β-aminoketone derivative 6-bromo-3-diethylaminomethyl-chroman-4-one). Inhibition of Spiro[cyclopentane-1,5'-[5H]dibenzo[a,d]cyclohepten]-2-one, 10',11'-t$_2$-10',11'-dihydro-3-methylene labeling was observed in the presence of Ub$_0$, concentrations blocking the MPTP. This latter finding is in line with the functional experiments reported above (see FIG. 5) and indicates that VDAC might represent the molecular target for ubiquinone inhibitors. CsA, AdNT ligands (ADP, BKA and ATR) and TFP did not affect the incorporation of radioactivity. Interestingly, the anion channel inhibitor DIDS, which has been shown to inhibit superoxide-induced VDAC-dependent cytochrome-c release from mitochondria (Madesh, M. & Hajnoczky, G. (2001) *J. Cell. Biol.* 155, 1003–1015), also appeared to inhibit the incorporation of Spiro[cyclopentane-1,5'-[5H]dibenzo[a,d]cyclohepten]-2-one,10',11'-t$_2$-10',11'-dihydro-3-methylene (FIG. 8B). Virtually identical results were obtained in affinity labeling experiments using liver mitochondria.

Example 14

Spiro[cyclopentane-1,5'-[5H]dibenzo[a,d]cyclohepten]-2-one, 10',11'-t$_2$-10',11'-dihydro-3-methylene-labeling in yeast mitochondria To further confirm VDAC1 as the protein target of Spiro[cyclopentane-1,5'-[5H]dibenzo[a,d]cyclohepten]-2-one, 10',11'-dihydro-3-methylene-, the labeling of proteins in mitochondria prepared from yeasts by Spiro[cyclopentane-1,5'-[5H]dibenzo[a,d]cyclohepten]-2-one,10',11'-t$_2$-10',11'-dihydro-3-methylene- was investigated. In strains in which the expression of major VDAC isoform in yeast, YVDAC1, had been eliminated by deletion of the por1 (Δpor1) gene, virtually no labeling was observed. However, yeast mitochondria prepared from Δpor1 strains containing plasmids, which mediate the expression of YVDAC1 showed prominent labeling of a 29 kDa band, the expected size of yeast VDAC, as confirmed by immunoblot analysis using an antibody raised against YVDAC1. Increasing concentration of unlabelled Spiro[cyclopentane-1,5'-[5H]dibenzo[a,d]cyclohepten]-2-one, 10',11'-dihydro-3-methylene-inhibited incorporation of the radioactivity (FIG. 9). Surprisingly, however, no clear labeling was observed in yeast mitochondria prepared from Δpor1 strains transformed with a plasmid mediating the expression of human VDAC1. This is spite of the fact that immunoblot analysis showed that the protein was indeed expressed.

TABLE 1

Effect of various inhibitors on $Ca^{2+}$-induced MPTP in rat liver mitochondria energised with succinate.

| Compounds | EC$_{50}$ (μM) |
|---|---|
| 3-methylene-chroman-4-one | 3.1 |
| 6-bromo-3-methylene-chroman-4-one | 1.2 |
| 6-chloro-3-methylene-chroman-4-one | 0.4 |
| 6,8-dichloro-3-methylene-chroman-4-one | 0.3 |
| Spiro[cyclopentane-1,5'-[5H]dibenzo[a,d]cyclohepten]-2-one,10',11'-dihydro-3-methylene- | 0.2 |
| Cyclosporin A | 0.3 |
| Ubiquinone$_0$ | 23.2 |
| ADP* | 4.8 |
| Bongkrekic acid | 11.5 |
| Trifluoroperazine | 9.4 |

*The experiments with ADP were performed in the presence of 1 μg/ml oligomycin.

The incubation medium contained 0.2 M sucrose, 10 mM Tris-Mops, pH 7.4, 1 mM Pi-Tris, 5 μM EGTA. Succinate (5 mM, in the presence of 2 μM rotenone) was used as respiratory substrate. After ~5 min incubation with the various compounds, swelling was induced by the addition of 80 μM $Ca^{2+}$ and A540 was monitored. EC$_{50}$ values were determined as percentage changes in absorbance at 540 nm (ΔA540) versus baseline (no CaCl$_2$), 20 min after the addition of CaCl$_2$, by fitting of the data to non-linear regression analysis using a four-parameters logistic equation using the SigmaPlot computer program.

The invention claimed is:
1. A method of modulating the activity of the MPTP complex in a biological sample comprising exposing said complex to a compound comprising general formula I,

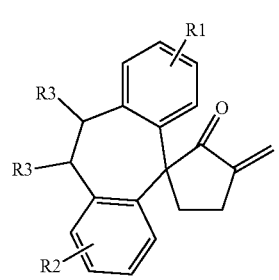

I wherein R1 and R2 are selected from the group consisting of H, halogen, alkyl, cycloalkyl, and alkoxy; and R3 is selected from the group consisting of H, D, and T.

2. The method of claim 1, wherein R1 and R2 are H and R3 is T.

3. A method of using a compound as an affinity label for a MPTP complex comprising exposing said complex to a compound of formula I,

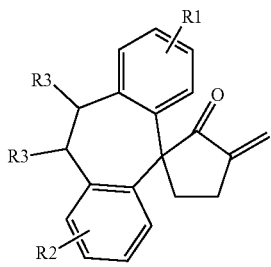

wherein R1 and R2 are selected from the group consisting of H, T, halogen, , alkyl, cycloalkyl, and alkoxy; and R3 is selected from the group consisting of H, D, and T, and wherein at least one of the residues R1, R2 and R3 further comprises at least one radioisotope.

4. The method of claim 3, wherein R1 and R2 are H and R3 is T.

5. A method for modulating the activity of a MPTP complex comprising: 1) exposing a cell or tissue in a biological sample to a compound comprising formula I

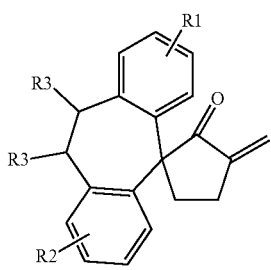

wherein R1 and R2 are selected from the group consisting of H, halogen, alkyl, cycloalkyl, and alkoxy, and R3 is selected from the group consisting of H, D, and T.

6. A method for determining the presence of a component of a MPTP complex comprising:
1) contacting a biological sample of interest with a compound comprising formula I,

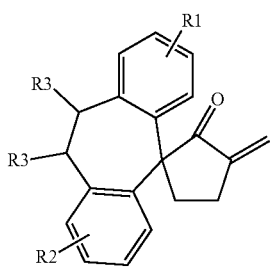

wherein R1 and R2 are selected from the group consisting of H, T, halogen, alkyl, cycloalkyl, and alkoxy; and R3 is selected from the group consisting of H, D, and T; and wherein at least one of the residues R1, R2 and R3 further comprises at least one radioisotope under conditions to permit the binding of the compound to a component of the MPTP complex; and
2) detecting the binding of the compound; and
3) optionally quantifying the binding of the compound detected.

7. A method for identifying an active agent that modulates the activity of a MPTP complex comprising:
1) contacting a biological sample containing cells with MPTP and a compound comprising formula I,

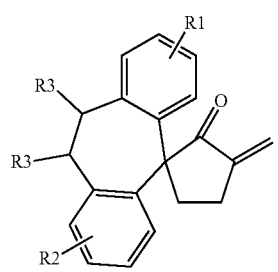

wherein R1 and R2 are selected from the group consisting of H, T, halogen, alkyl, cycloalkyl, and alkoxy; and R3 is selected from the group consisting of H, D, and T; and wherein at least one of the residues R1, R2 and R3 further comprises at least one radioisotope in the presence of a candidate agent; and
2) comparing the binding of the compound to MPTP in the presence of the candidate agent with the binding of the compound to MPTP in the absence of said agent; and 3) optionally, testing the activity of said selected agent on the MPTP activity in a preparation of a cellular extract comprising subcellular elements with MPTP.

8. A method for identifying an active agent that modulates the activity of a MPTP complex by interacting with VDAC1 comprising:
1) contacting a biological sample containing cells with VDAC1 of the MPTP complex with a compound comprising formula I,

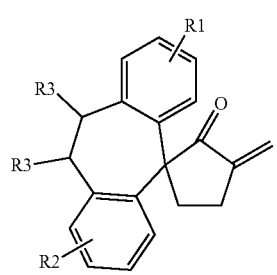

wherein R1 and R2 are selected from the group consisting of H, T, halogen, alkyl, cycloalkyl, and alkoxy; and R3 is selected from the group consisting of H, D, and T; wherein at least one of the residues R1, R2 and R3 comprises at least one radioisotope in the presence of a candidate agent; and
2) comparing the binding of the compound to VDAC1 of the MPTP complex in the presence of the candidate agent with the binding of the compound to VDAC1 of the MPTP complex in the absence of said agent; and 3)

optionally, testing the activity of said selected agent on the MPTP activity in a preparation of a cellular extract comprising subcellular elements with VDAC1 of the MPTP complex.

9. A compound of general formula I

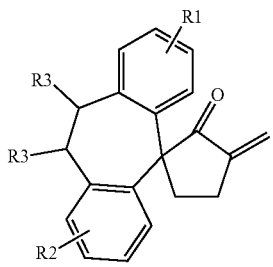

wherein R1 and R2 are selected from the group consisting of H, halogen, alkyl, cycloalkyl, and alikoxy; and R3 is selected from the group consisting of H, D, and T.

10. The compound of claim 9, wherein at least one of the residues R1, R2 and R3 further comprises at least one radioisotope.

11. The compound of claim 9, wherein the compound is a compound of formula I wherein R1 and R2 are H and R3 is T.

12. The compound of claim 9 wherein said compound is a modulator of the activity of the MPTP complex.

13. The compound of claim 9 wherein said compound is an affinity label.

14. The compound of claim 9 wherein said compound is an affinity label for a component of the MPTP complex.

* * * * *